US010383916B2

(12) United States Patent
Crystal et al.

(10) Patent No.: US 10,383,916 B2
(45) Date of Patent: Aug. 20, 2019

(54) ANGIOGENIC CONDITIONING TO ENHANCE CARDIAC CELLULAR REPROGRAMMING OF FIBROBLASTS OF THE INFARCTED MYOCARDIUM

(71) Applicants: Cornell University, Ithaca, NY (US); The Research Foundation For The State University Of New York, Albany, NY (US)

(72) Inventors: Ronald G. Crystal, New York, NY (US); Todd K. Rosengart, Bellaire, TX (US); Robert Gersch, Philadelphia, PA (US); Megumi Mathison, Houston, TX (US)

(73) Assignees: CORNELL UNIVERSITY, Ithaca, NY (US); THE RESEARCH FOUNDATION FOR THE STATE UNIVERSITY OF NEW YORK, Albany, NY (US)

(*) Notice: Subject to any disclaimer, the term of this patent is extended or adjusted under 35 U.S.C. 154(b) by 0 days.

(21) Appl. No.: 14/439,357

(22) PCT Filed: Nov. 1, 2013

(86) PCT No.: PCT/US2013/068086
§ 371 (c)(1),
(2) Date: Apr. 29, 2015

(87) PCT Pub. No.: WO2014/071199
PCT Pub. Date: May 8, 2014

(65) Prior Publication Data
US 2015/0290290 A1 Oct. 15, 2015

Related U.S. Application Data

(60) Provisional application No. 61/721,604, filed on Nov. 2, 2012.

(51) Int. Cl.
| | | |
|---|---|---|
| A61K 48/00 | (2006.01) | |
| C12N 15/867 | (2006.01) | |
| C12N 15/861 | (2006.01) | |
| C12N 15/18 | (2006.01) | |
| A61K 38/18 | (2006.01) | |
| C07K 14/47 | (2006.01) | |
| C07K 14/515 | (2006.01) | |
| C07K 14/52 | (2006.01) | |
| A61K 38/17 | (2006.01) | |
| C07K 14/49 | (2006.01) | |
| A61K 38/00 | (2006.01) | |

(52) U.S. Cl.
CPC ...... *A61K 38/1866* (2013.01); *A61K 38/1709* (2013.01); *A61K 48/00* (2013.01); *A61K 48/005* (2013.01); *C07K 14/47* (2013.01); *C07K 14/49* (2013.01); *C07K 14/52* (2013.01); *A61K 38/00* (2013.01); *C12N 2710/10341* (2013.01); *C12N 2740/15041* (2013.01)

(58) Field of Classification Search
None
See application file for complete search history.

(56) References Cited

U.S. PATENT DOCUMENTS

| | | | |
|---|---|---|---|
| 4,797,368 A | 1/1989 | Carter et al. | |
| 2003/0113301 A1* | 6/2003 | Edge | C12N 5/0656 424/93.21 |
| 2008/0081354 A1 | 4/2008 | Qu et al. | |
| 2010/0166714 A1* | 7/2010 | Chien | C12N 5/0657 424/93.7 |
| 2012/0009158 A1* | 1/2012 | Chien | A61K 35/34 424/93.7 |
| 2012/0157381 A1* | 6/2012 | Spees | A61K 35/34 514/8.1 |

FOREIGN PATENT DOCUMENTS

| | | |
|---|---|---|
| WO | WO 02/12539 A2 | 2/2002 |
| WO | WO 2009/145761 A1 | 12/2009 |
| WO | WO 2011/139688 A2 | 11/2011 |

OTHER PUBLICATIONS

Wolfram et al, Gene Therapy to Treat Cardiovascular Disease, Journal of the American Heart Association, 2013, pp. 1-11.*
Mathison et al, In Vivo Cardiac Cellular Reprogramming Efficacy Is Enhanced by Angiogenic Preconditioning of the Infarcted Myocardium With Vascular Endothelial Growth Factor, Journal of the American Heart Association, 2012, pp. 1-14.*
Qian et al, In vivo reprogramming of murine cardiac fibroblasts into induced cardiomyocytes, Nature. May 31, 2012; 485(7400): 593-598.*
Chen et al, Stimulation of adult resident cardiac progenitor cells by durable myocardial expression of thymosin beta 4 with ultrasound-targeted microbubble delivery, Gene Therapy (2013) 20, 225-233; published online Nov. 15, 2012.*
Chen et al, Adeno-associated virus vectors simultaneously encoding VEGF and angiopoietin-1 enhances neovascularization in ischemic rabbit hindlimbs, Acta Pharmacol Sin Apr. 2007; 28 (4): 493-502.*

(Continued)

Primary Examiner — Maria Marvich
(74) Attorney, Agent, or Firm — Leydig, Voit & Mayer, Ltd.

(57) ABSTRACT

Provided is a method of treating coronary artery disease in a mammal, comprising administering to a region of the heart of the mammal (a) a first vector encoding one or more angiogenic proteins which induce vascularization in the heart of the mammal, and (b) a second vector encoding one or more cardio-differentiating transcription factors which induce the production of induced cardiomyocytes (iCM) in the heart of the mammal, whereby the coronary artery disease in the mammal is treated. In a preferred embodiment, the first vector is an adenoviral vector encoding VEGF and the second vector is a lentiviral vector encoding Gata4, Mef2c, and Tbx5 (GMT).

10 Claims, 19 Drawing Sheets
Specification includes a Sequence Listing.

(56) References Cited

OTHER PUBLICATIONS

Amano et al., Alteration of Splicing Signals in a Genomic/cDNA Hybrid VEGF Gene to Modify the Ratio of Expressed VEGF Isoforms Enhances Safety of Angiogenic Gene Therapy, *Molecular Therapy*, 12(4): 716-724 (2005).
Anyanwu et al., Prognosis after heart transplantation, *Brit. Med. J.*, 326: 509-510 (2003).
Apostolou et al., iPS cells under attack, *Nature*, 474: 165-166 (2011).
Ausubel et al., *Current Protocols in Molecular Biology*, Greene Publishing Associates and John Wiley & Sons, New York, N.Y. (1994) (Table of Contents only).
Berns "Parvoviridae and Their Replication" in *Fundamental Virology*, 2nd Edition pp. 817-837 (B. N. Fields and D. M. Knipe, eds.) (1991).
Boshart et al., A Very Strong Enhancer Is Located Upstream of an Immediate Early Gene of Human Cytomegalovirus, *Cell*, 41: 521-530 (1985).
Chen et al., *Circ. Res.*, 111(1): 50-55 (2012).
Chen et al., Vascular endothelial growth factor promotes cardiomyocyte differentiation of embryonic stem cells, *Am. J. Physiol. Heart Circ. Physiol.*, 291: H1653-H1658 (2006).
Chu et al., SV40 DNA transfection of cells in suspension: analysis of the efficiency of transcription and translation of T-antigen, *Gene*, 13: 197-202 (1981).
Claes et al., Another angiogenesis-independent role for VEGF: SDF1-dependent cardiac repair via cardiac stern cells *Cardiovascular Research*, 91(3): 369-370 (2011).
Daskalopoulos et al., Myofibroblasts in the Infarct Area: Concepts and Challenges. *Microsc. Microanal.*, 18(1): 35-49 (2012).
Davis et al., *Basic Methods in Molecular Biology*, Elsevier (1986) (Table of Contents only).
Durand et al., The Inside Out of Lentiviral Vectors, *Viruses*, 3(2): 132-159 (2011).
Efe et al., Conversion of mouse fibroblasts into cardiomyocytes using a direct reprogramming strategy, *Nature Cell Biology*, 13(3): 215-222 (2011).
Fedak et al., Cell Therapy Limits Myofibroblast Differentiation and Structural Cardiac Remodeling, *Circ. Heart Failure*, 5(3): 349-356 (2012).
Felgner et al., Lipofection: A highly efficient, lipid-mediated DNA-transfection procedure, *Proc. Natl. Acad. Sci. USA*, 84: 7413-7417 (1987).
Gai et al., Generation and characterization of functional cardiomyocytes using induced pluripotent stem cells derived from human fibroblasts, *Cell Biology International*, 33(11): 1184-1193 (2009).
Galfre et al., Preparation of Monoclonal Antibodies: Strategies and Procedures, *Methods in Enzymology*, 73: 3-46 (1981).
Graham et al., A New Technique for the Assay of Infectivity of Human Adenovirus 5 DNA, *Virology*, 52: 456-467 (1973).
Graham et al., Characteristics of a Human Cell Line Transformed by DNA from Human Adenovirus Type 5, *J. Gen. Virol.*, 36: 59-72 (1977).
Hare et al., Cardiac regeneration and stem cell therapy, *Curr. Opin. Organ Transplant*, 13(5): 536-542 (2008).
Ieda et al., Direct Reprogramming of Fibroblastsinto Functional Cardiomyocytes by Defined Factors, *Cell*, 142(3): 375-386 (2010).
Jayawardena et al., MicroRNA-Mediated In Vitro and In Vivo Direct Reprogramming of Cardiac Fibroblasts to Cardiomyocytes, *Circulation Research*, 110(11): 1465-1473 (2012).
Klein et al., High-velocity microprojectiles for delivering nucleic acids into living cells, *Nature*, 327: 70-73 (1987).
Kotin et al., Prospects for the Use of Adeno-Associated Virus as a Vector for Human Gene Therapy, *Human Gene Therapy*, 5: 793-801 (1994).
Ladner et al., Human CSF-1: gene structure and alternative splicing of mRNA precursors, *The EMBO Journal*, 6(9): 2693-2698 (1987).
Laflamme et al., Cardiomyocytes derived from human embryonic stem cells in pro-survival factors enhance function of infracted rat hearts, *Nature Biotechnology*, 25(9): 1015-1024 (2007).
Leor et al., Transplantation of fetal myocardial tissue into the infarcted myocardium of rat. A potential method for repair of infarcted myocardium?, *Circulation*, 94(Suppl. 9): II332-II336 (1996).
Lietz et al., Outcomes of Left Ventricular Assist Device Implantation as Destination Therapy in the Post-REMATCH Era, *Circulation*, 116(5): 497-505 (2007).
Lloyd-Jones et al., Heart Disease and Stroke Statistics-2009 Update a Report From the American Heart Association Statistics Committee and Stroke Statistics Subcommittee, *Circulation*, 119(3): 480-486 (2009).
Mauritz et al., Generation of Functional Murine Cardiac Myocytes From Induced Pluripotent Stem Cells, *Circulation*, 118(5): 507-517 (2008).
Mannino et al., Liposome Mediated Gene Transfer, *Bio Techniques*, 6(7): 682-690 (1988).
Mathison et al., In Vivo Cardiac Cellular Reprogramming Efficacy Is Enhanced by Angiogenic Preconditioning of the Infarcted Myodarcium with Vascular Endothelial Growth Factor, *Journal of the American Heart Association*, 1(6): e005652-e005652 (2012).
McKnight et al., The Distal Transcription Signals of the Herpesvirus tk gene Share a Commom Hexanucleotide Control Sequence, *Cell*, 37: 253-262 (1984).
Menasche, Cardiac cell therapy: Lessons from clinical trials, *Journal of Molecular and Cellular Cardiology*, 50(2): 258-265 (2010).
Min et al., Transplantation of embryonic stem cells improves cardiac function in postinfarcted rats, *J. Appl. Physiol.*, 92(1): 288-296 (2002).
Mummery, Induced Pluripotent Stem Cells—A Cautionary Note, *The New England Journal of Medicine*, 364(22): 2160-2162 (2011).
Murry et al., Regeneration Gaps Observations on Stem Cells and Cardiac Repair, *Journal of the American College of Cardiology*, 47(9): 1777-1785 (2006).
Narazaki et al., Directed and Systematic Differentiation of Cardiovascular Cells From Mouse Induced Pluripotent Stem Cells, *Circulation*, 118(5): 498-506 (2008).
Nelson et al., Repair of Acute Myocardial Infarction by Human Sternness Factors Induced Pluripotent Stem Cells, *Circulation*, 120(5): 408-416 (2009).
Ng et al., Evolution of the Functional Human β-Actin Gene and Its Multi-Pseudogene Family: Conservation of Noncoding Regions and Chromosomal Dispersion of Pseudogenes, *Molecular and Cellular Biology*, 5(10): 2720-2732 (1985).
Okita et al., Generation of germline-competent induced pluripotent stem cells, *Nature*, 448: 313-317 (2007).
Okita et al., Immunogenicity of Induced Pluripotent Stem Cells, *Circulation Research*, 109(7): 720-721 (2011).
Orlic et al., Bone marrow cells regenerate infarctedmyocardium, *Nature*, 410(6829): 701-704 (2001).
Passier et al., Getting to the Heart of the Matter: Direct Reprogramming to Cardiomyocytes, *Cell Stem Cell*, 7(2): 139-141 (2010).
Protze et al., A new approach to transcription factor screening for reprogramming of fibroblasts to cardiomyocyte-like cells, *Journal of Molecular and Cellular Cardiology*, 53(3): 323-332 (2012).
Qian et al., In vivo reprogramming of murine cardiac fibroblasts into induced cardiomyocytes, *Nature*, 485(7400): 593-598 (2012).
Reinecke et al., Survival, Integration, and Differentiation of Cardiomyocyte Grafts, A Study in Normal and Injured Rat Hearts, *Circulation*, 100(2): 193-202 (1999).
Retuerto et al., Angiogenic pretreatment improves the efficacy of cellular cardiomyoplasty performed with fetal cardiomyocyte implantation, *The Journal of Thoracic and Cardiovascular Surgery*, 127(4): 1041-1049 (2004).
Retuerto et al., Angiogenic pretreatment to enhance myocardial function after cellular cardiomyoplasty with skeletal myoblasts, *The Journal of Thoracic and Cardiovascular Surgery*, 133(2): 478-484 (2007).
Rosenzweig, Cardiac Cell Therapy-Mixed Results from Mixed Cells, *The New England Journal of Medicine.*, 355(12): 1274-1277 (2006).
Sambrook et al., *Molecular Cloning, a Laboratory Manual*, 2d edition, Cold Spring Harbor Press, Cold Spring Harbor, N.Y. (1989) (Table of Contents only).

(56) References Cited

OTHER PUBLICATIONS

Santos Coura et al., The state of the art of adeno-associated virus-based vectors in gene therapy, *Virology Journal*, 4(99):1-7 (2007).

Scorsin et al., Comparison of the Effects of Fetal Cardiomyocyte and Skeletal Myoblast Transplantation on Postinfarction Left Ventricular Function, *The Journal of Thoracic and Cardiovascular Surgery.*, 119(6): 1169-1175 (2000).

Shigekawa et al., Electroporation of Eukaryotes and Prokaryotes: A general Approach to the Introduction of Macromolecules into Cells, *BioTechniques*, 6(8): 742-751 (1988).

Song et al., Heart repair by reprogramming non-myocytes with cardiac transcription factors, *Nature*, 485(7400): 599-604 (2012).

Song et al., VEGF is critical for spontaneous differentiation of stem cells into cardiomyocytes, *Biochemical and Biophysical Research Communications*, 354(4): 999-1003 (2007).

Srivastava et al., Critical Factors for Cardiac Reprogramming, *Circulation Research*, 111(1): 5-8 (2012).

Takahashi et al., Induction of Pluripotent Stem Cells from Adult Human Fibroblasts by Defined Factors, *Cell*, 131(5): 861-872 (2007).

Taylor et al., The Registry of the International Society for Heart and Lung Transplantation: Twenty-first Official Adult Heart Transplant Report—2004, *The Journal of Heart and Lung Transplantation*, 23(7): 796-803 (2004).

Taylor et al., Regenerating functional myocardium: Improved performance after skeletal myoblast transplantation, *Nature Medicine*, 4(8): 929-933 (1998).

Tomita et al., Autologous Transplantation of Bone Marrow Cells Improves Damaged Heart Function, *Circulation*, 100(Suppl. 19): II247-II256 (1999).

Urlaub et al., Isolation of Chinese hamster cell mutants deficient in dihydrofolate reductase activity, *Proc. Natl. Acad. Sci. (USA)*, 77(7): 4216-4220 (1980).

Van Den Borne et al., Myocardial remodeling after infarction: the role of myofibroblasts, *Nature Reviews Cardiology*, 7(1): 30-37 (2010).

Xu et al., Phenotypic correction of murine hemophilia A using an iPS cell-based therapy, *Proc. Natl. Acad. Sci. (USA)*, 106(3): 808-813 (2009).

Yang et al., VEGF enhances functional improvement of postinfarcted hearts by transplantation of ESC-differentiated cells, *J. Appl. Physiol.*, 93(3): 1140-1151 (2002).

Yu et al., Induced Pluripotent Stem Cell Lines Derived from Human Somatic Cells, *Science*, 318(5858): 1917-1920 (2007).

Zhang et al., Functional Cardiomyocytes Derived From Human Induced Pluripotent Stem Cells, *Circulation Research*, 104(4): e30-e41 (2009).

Zhang et al., Collagen-Targeting Vascular Endothelial Growth Factor Improves Cardiac Performance After Myocardial Infarction, *Circulation*, 119(13): 1776-1784 (2009).

Zhang et al., Cardiomyocyte Grafting for Cardiac Repair: Graft Cell Death and Anti-Death Strategies, *J. Mol. Cell. Cardiol.*, 33(5): 907-921 (2001).

Zhao et al., Immunogenicity of induced pluripotent stem cells, *Nature*, 474(7350): 212-214 (2011).

Haider et al., "Angiomyogenesis for myocardial repair", *Antioxidants & redox signaling*, 11(8): 1929-1944 (2009).

* cited by examiner

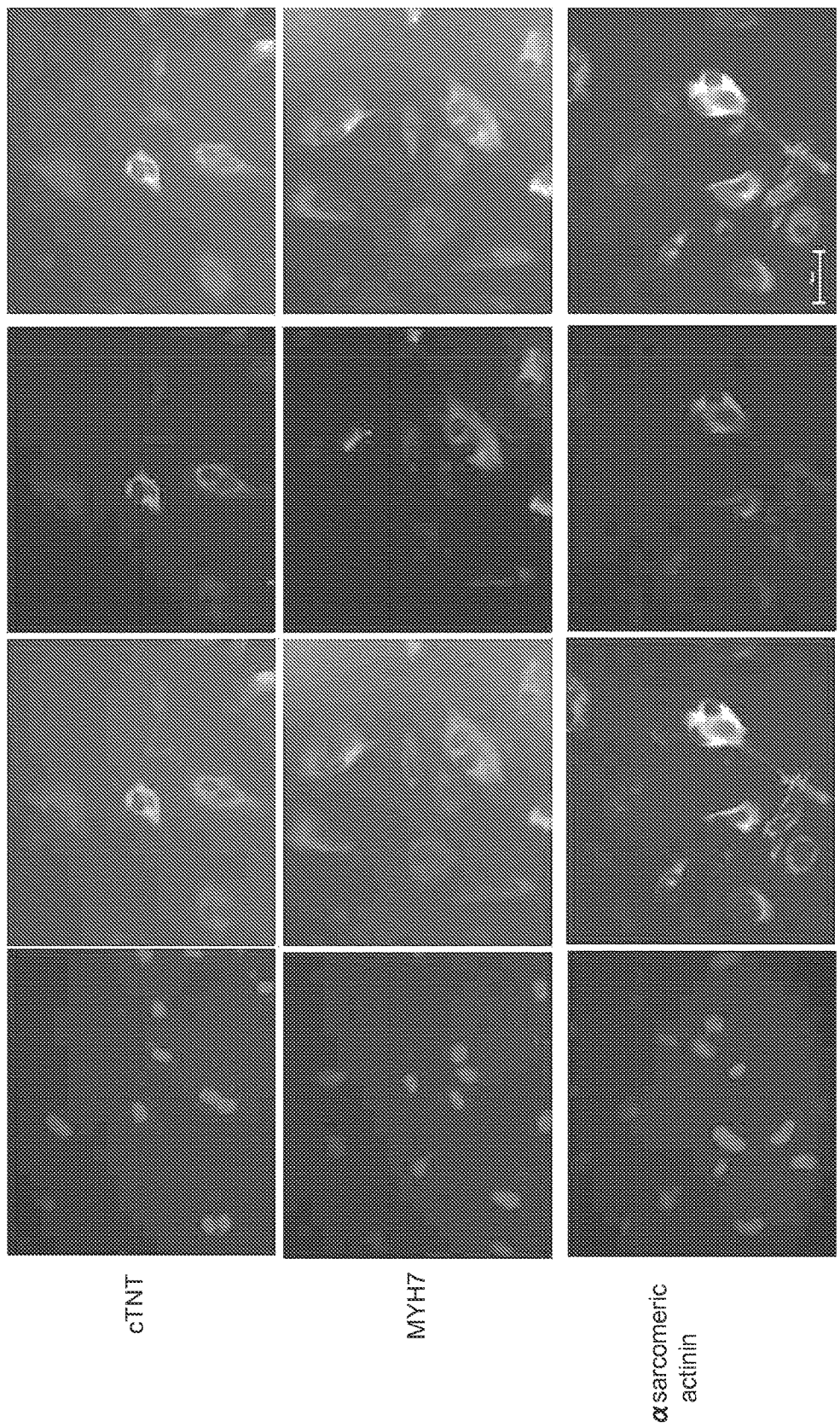

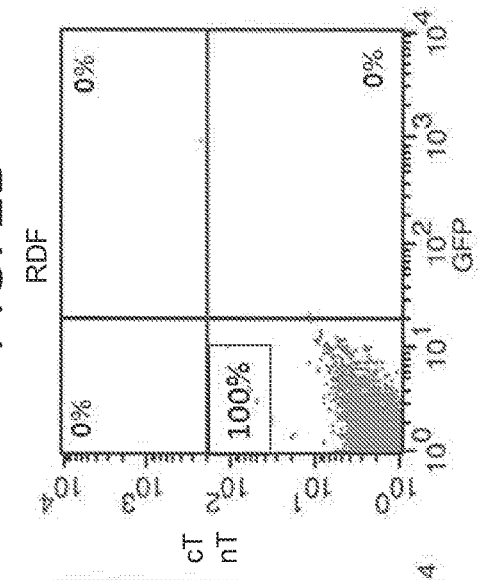
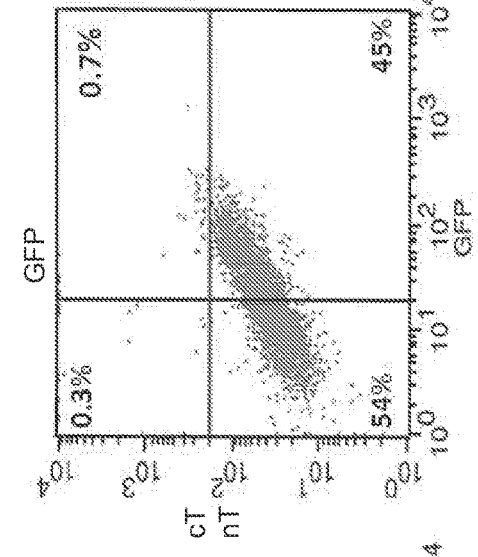
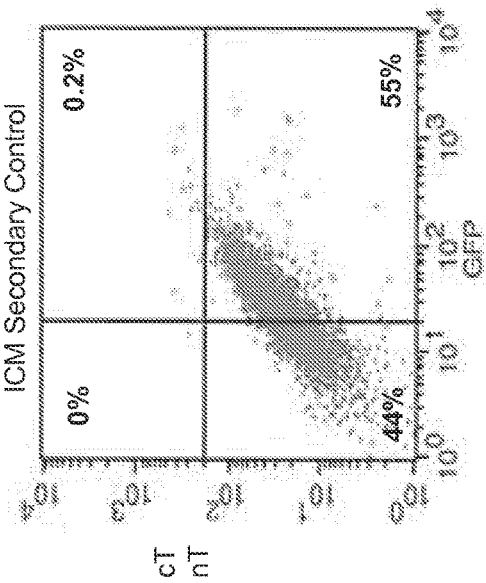
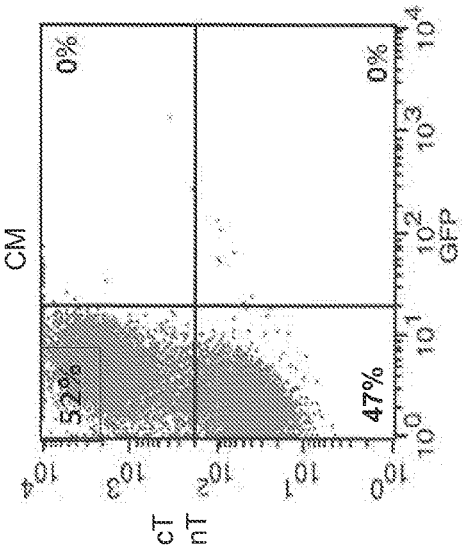

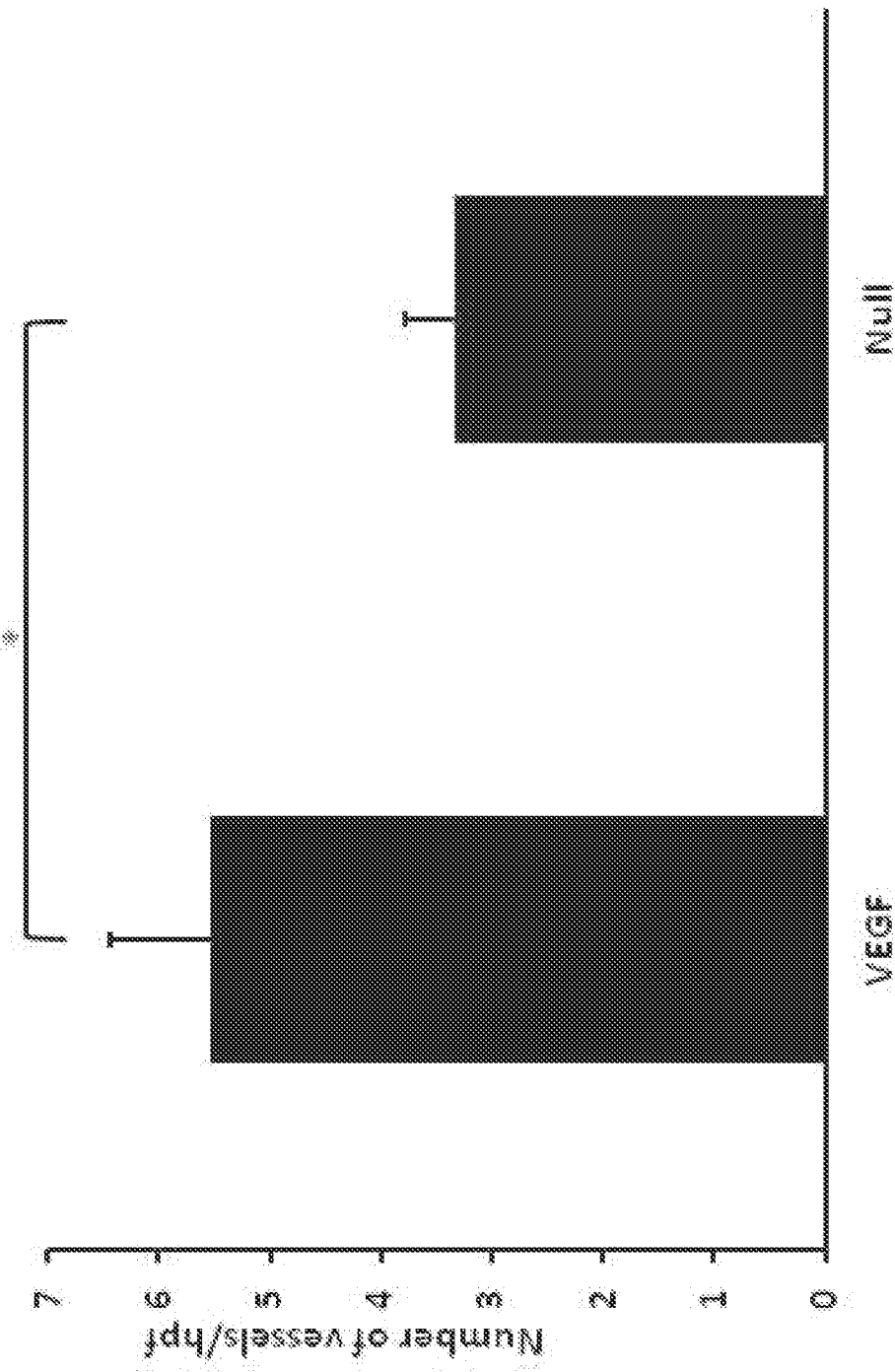

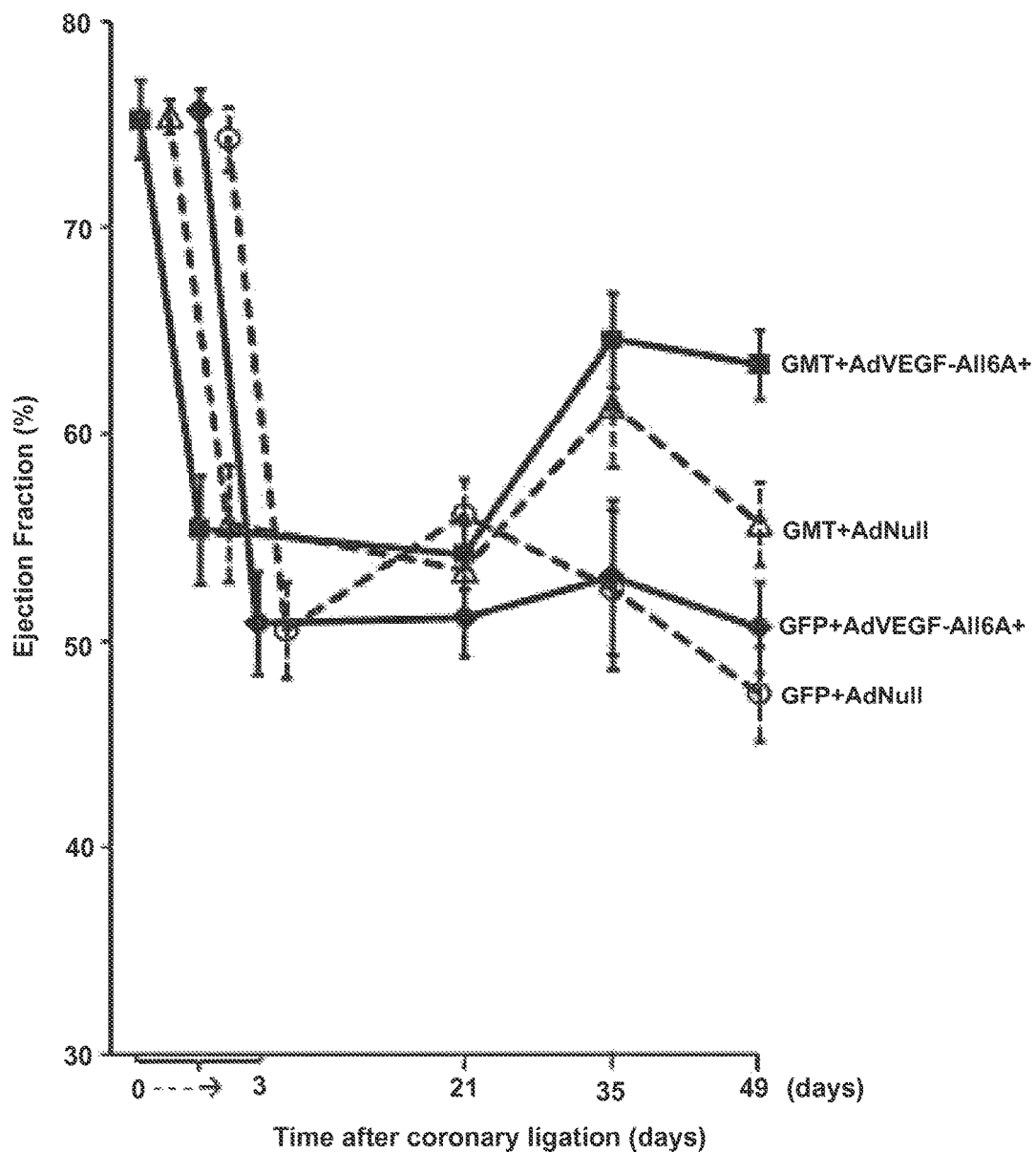

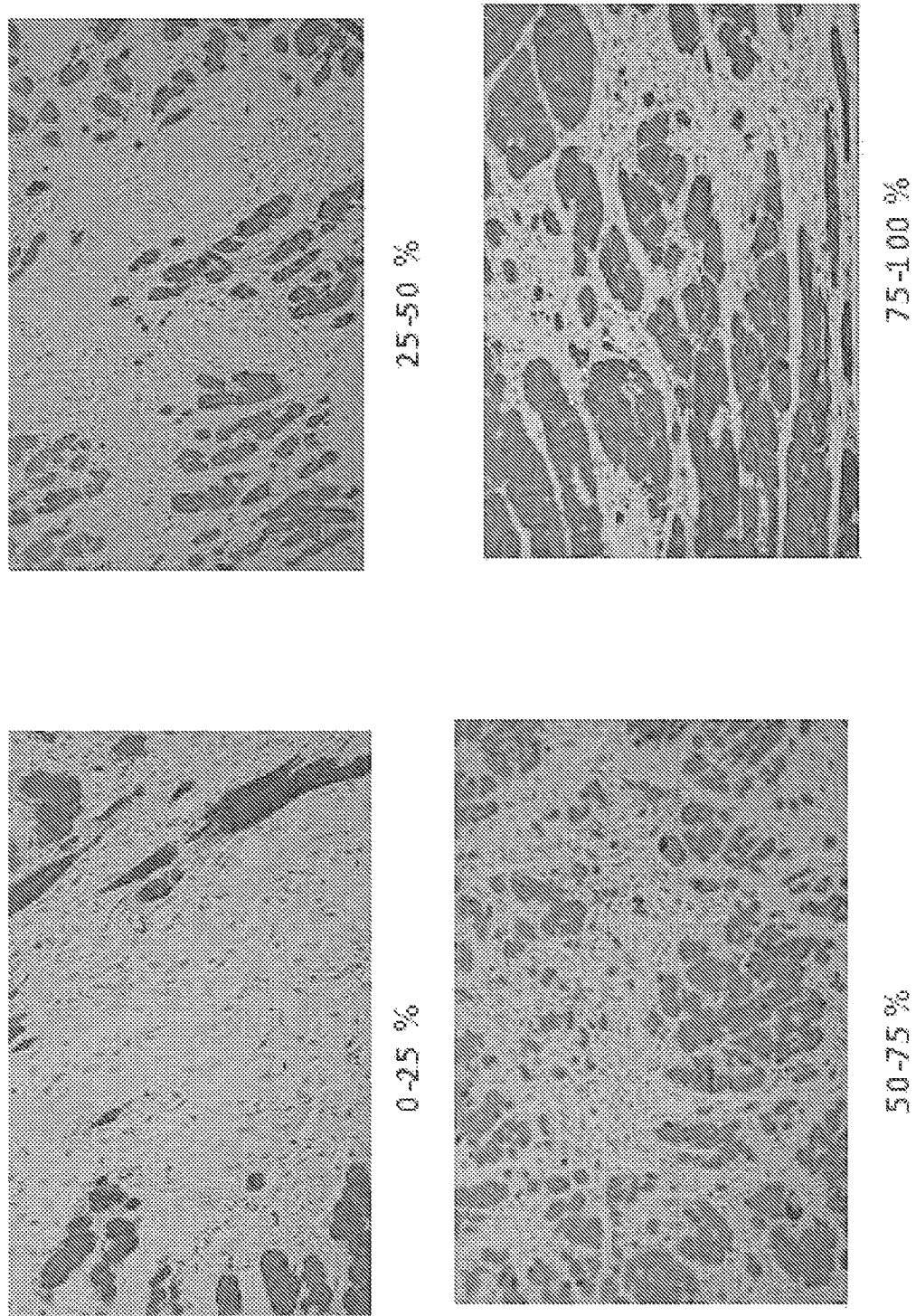

FIG. 8
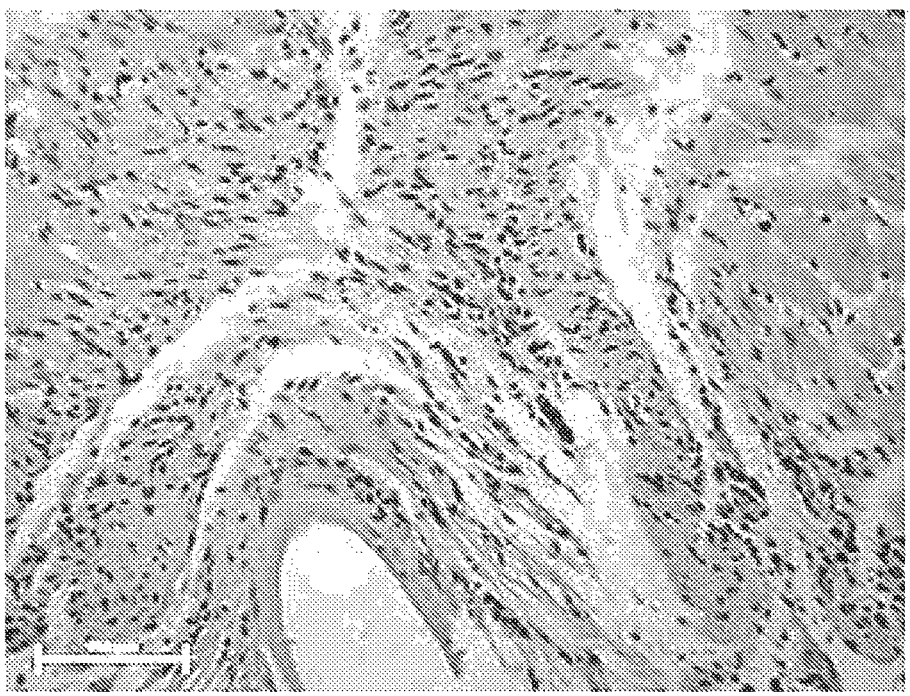
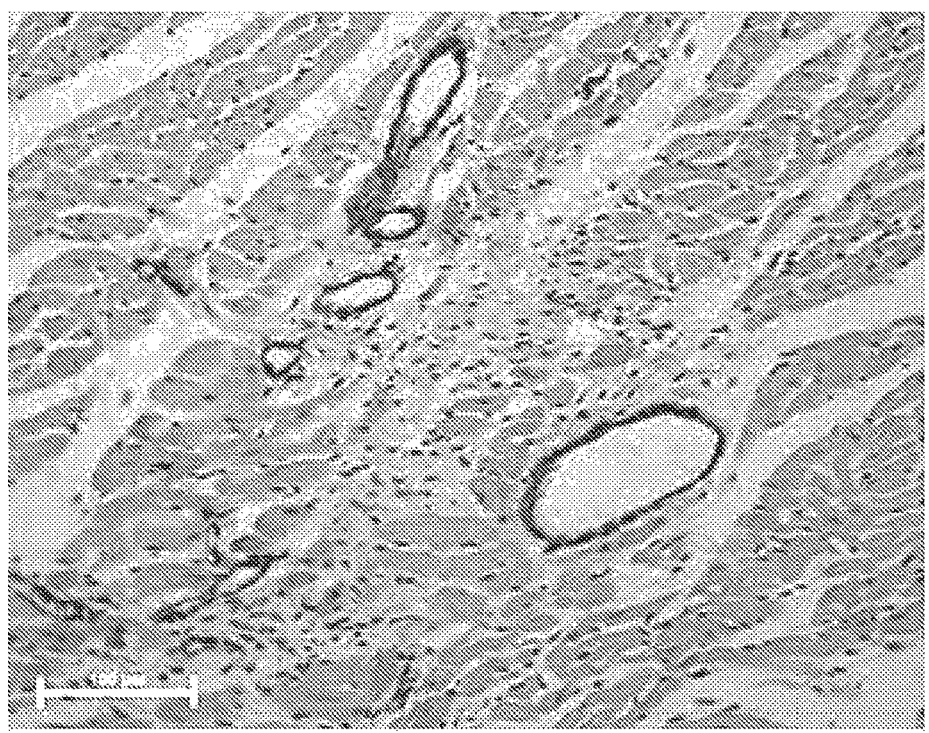

FIG. 9
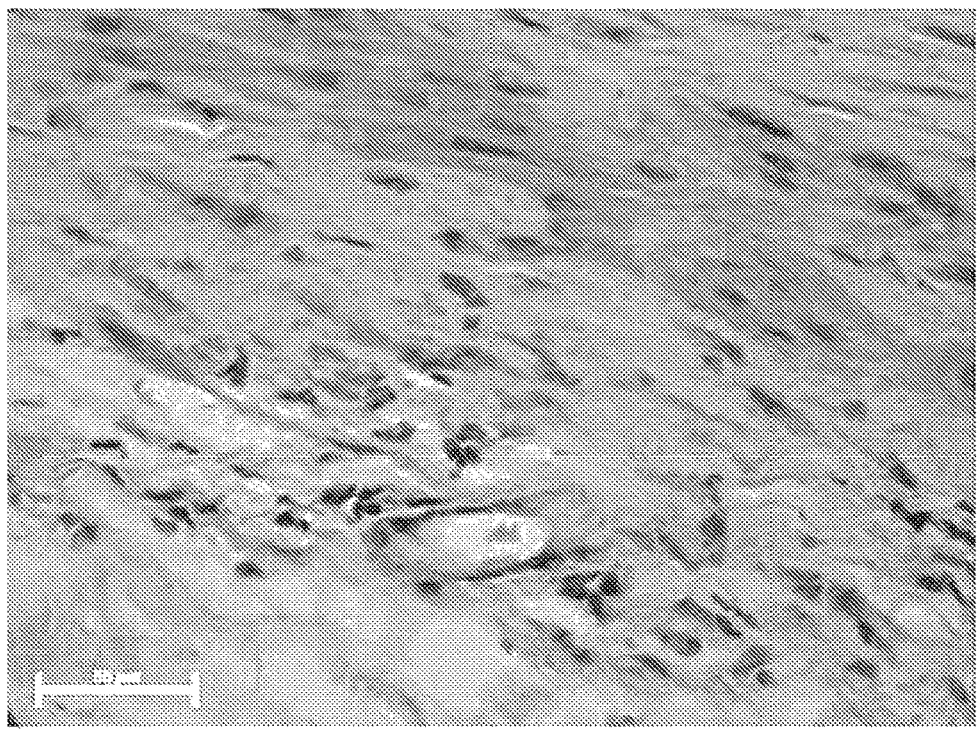

FIG. 10A
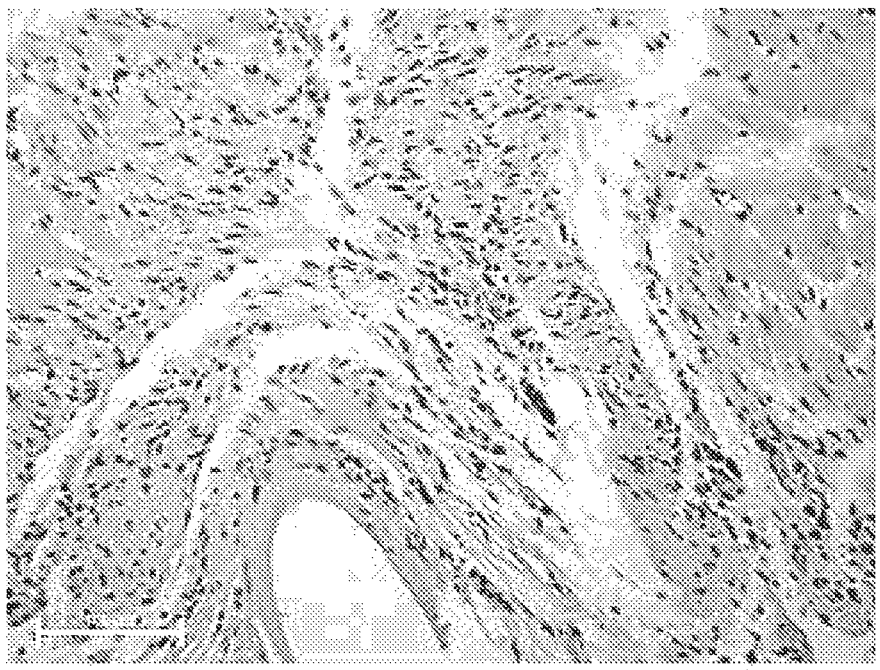
AdNull/GFP
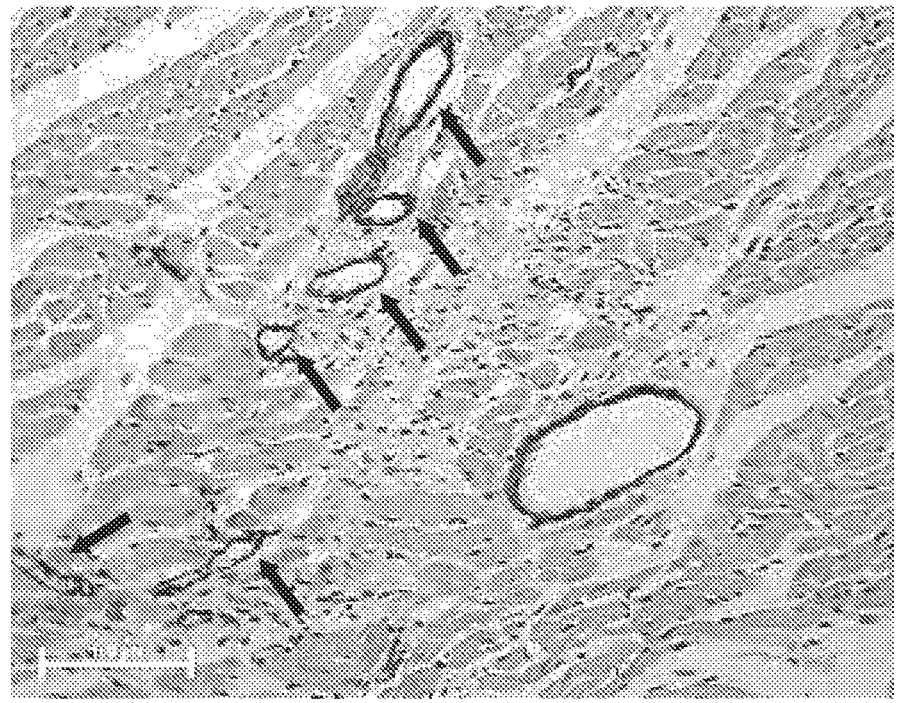
VEGF/GMT

FIG. 11A
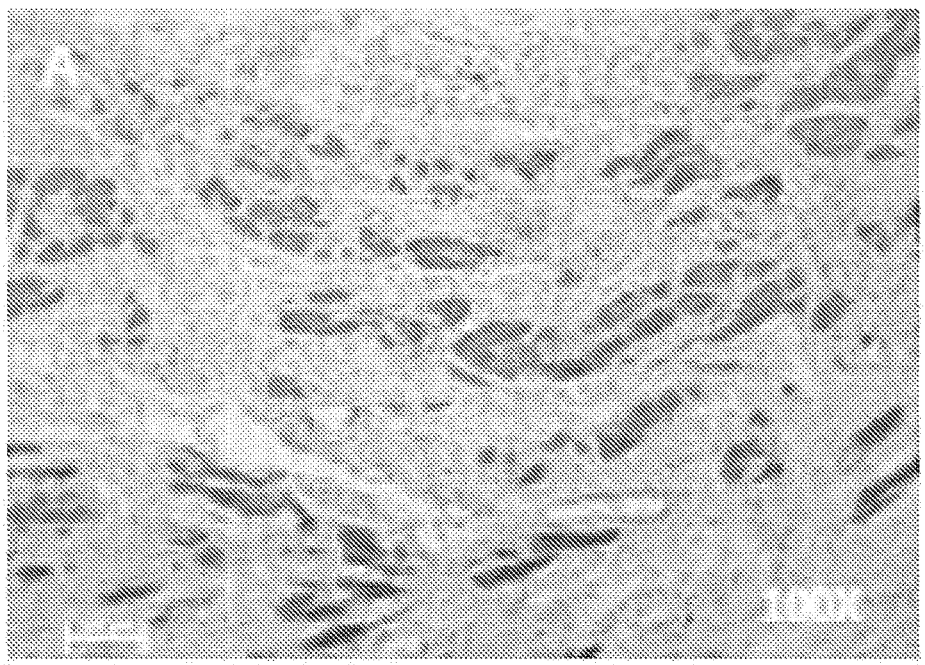
AdNull
GFP
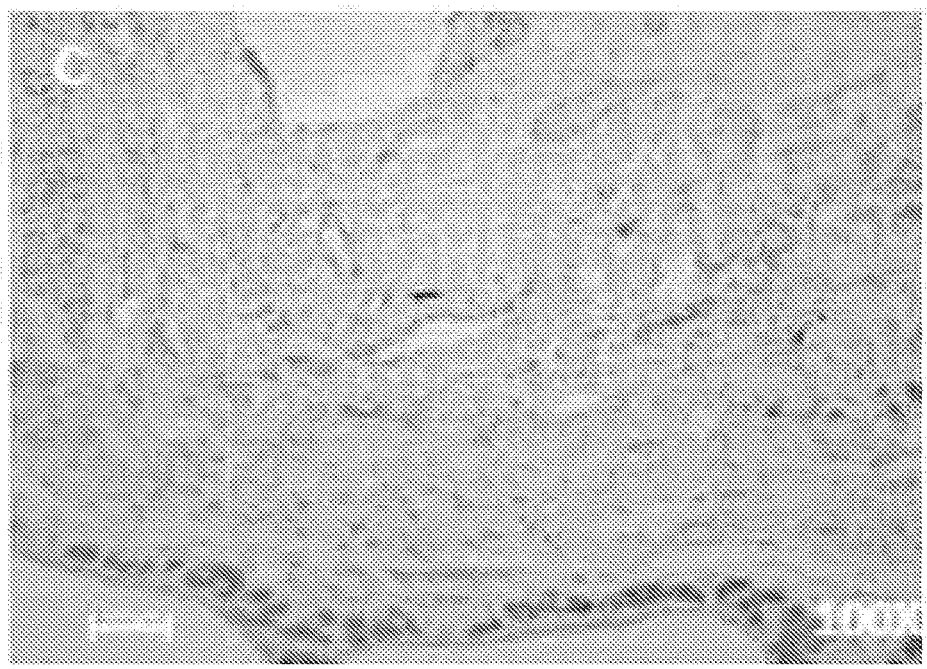
AdNull
GFP

ND GIOGENIC CONDITIONING TO
ENHANCE CARDIAC CELLULAR
REPROGRAMMING OF FIBROBLASTS OF
THE INFARCTED MYOCARDIUM

CROSS-REFERENCE TO RELATED
APPLICATIONS

This patent application claims the benefit of U.S. Provisional Patent Application No. 61/721,604, filed Nov. 2, 2012, which is incorporated by reference in its entirety herein.

INCORPORATION-BY-REFERENCE OF
MATERIAL SUBMITTED ELECTRONICALLY

Incorporated by reference in its entirety herein is a computer-readable nucleotide/amino acid sequence listing submitted concurrently herewith and identified as follows: One 1,555 Byte ASCII (Text) file named 720562 ST25.TXT created on Apr. 23, 2015.

BACKGROUND OF THE INVENTION

Coronary artery disease (CAD) remains the leading cause of death in the West, in part because of the still limited options for the treatment of diffuse CAD, myocardial infarction and congestive heart failure (Lloyd-Jones et al., *Circulation*, 119(3): 480-486 (2009); Taylor et al., *J. Heart Lung Transplant*, 23(7): 796-803 (2004); Lietz et al., *Circulation*, 116(5): 497-505 (2007); Anyanwu et al., *Brit. Med. J.*, 326(7388): 509-510 (2003)). Cardiac stem cell therapy has been embraced as a new approach to treating end-stage heart disease that theoretically repopulates otherwise permanently scarred myocardium with contractile cells (Leor et al., *Circulation*, 94(Suppl. 9): II332-II336 (1996); Taylor et al., *Nature Med.*, 4(8): 929-933 (1998); Tomita et al., *Circulation*, 100(Suppl. 19): II247-II256 (1999); Orlic et al., *Nature*, 410(6829): 701-704 (Apr. 5, 2001); Scorsin et al., *J. Thorac. Cardiovasc. Surg.*, 119(6): 1169-1175 (2000); Hare et al., *Curr. Opin. Organ Transplant*, 13(5): 536-542 (2008); Rosenzweig, *N. Engl. J. Med.*, 355(12): 1274-1277 (2006); Murry et al., *J. Am. Coll. Cardiol.*, 47(19): 1777-85 (2006); Menasche, *J. Mol. Cell. Cardiol.*, 50(2): 258-265 (2010)). The creation of induced pluripotent stem cells (iPSCs) and the generation of cardiomyocyte-like cells from iPSCs appear to have represented breakthroughs in this field (Min et al., *J. Appl. Phys.*, 92(1): 288-296 (2002); Takahashi et al., *Cell*, 131(5): 861-872 (2007); Yu et al., *Science*, 318(5858): 1917-1920 (2007); Okita et al., *Nature*, 448(7151): 313-317 (2007); Xu et al., *Proc. Natl. Acad. Sci.* (USA), 106(3): 808-813 (2009); Gai et al., *Cell Biol. Intl.*, 33(11): 1184-1193 (2009); Mauritz et al., *Circulation*, 118(5): 507-517 (2008); Nelson et al., *Circulation*, 120(5): 408-416 (2009); Narazaki et al., *Circulation*, 118(5): 498-506 (2008); Zhang et al., *Circ Res.*, 104(4): e30-e41 (2009)), but recent reports of iPSC tumorogenicity and immunogenicity may ultimately reflect limits to the clinical applicability of iPSCs, as may the logistic challenges of iPSC delivery in the clinical setting (Okita et al., *Circ Res.*, 109(7): 720-721 (2011); Apostolou et al., *Nature*, 474(7350): 165 (2011); Mummery, *N. Engl. J. Med.*, 364(22): 2160-2162 (2011); Zhao et al., *Nature*, 474(7350): 212-214 (2011)).

The recent discovery that a trio of cardio-differentiating transcription factors could be used to generate induced cardiomyocytes (iCM) directly from somatic cells (Ieda et al., *Cell*, 142(3): 375-386 (2010)) offers the exciting new possibility of generating autologous cells that possess characteristics that are at least consistent with that of a cardiomyocyte phenotype (Ieda et al., *Cell*, 142(3): 375-386 (2010); Efe et al., *Nature Cell. Bio.*, 13(3): 215-222 (2011); Qian et al., *Nature*, 485(7400): 593-598 (2012); Passier et al., *Cell Stem Cell*, 7(2): 139-141 (2010); Song et al., *Nature*, 485(7400): 599-604 (2012); Srivastava et al., *Circ. Res.*, 111(1): 5-8 (2012); Jayawardena et al., *Circ. Res.*, 110(11): 1465-1473 (2012); Protze et al., *J. Mol. Cell. Cardiol.*, 53(3): 323-332 (2012)). Perhaps more importantly, this novel regenerative strategy offers the intriguing potential to bypass iPSC staging and convert myocardial scar fibroblasts into functional iCM in situ, potentially transforming regions of myocardial infarction back into functioning myocardium (Qian et al., *Nature*, 485(7400): 593-598 (2012); Song et al., *Nature*, 485(7400): 599-604 (2012); Srivastava et al., *Circ. Res.*, 111(1): 5-8 (2012); Jayawardena et al., *Circ. Res.*, 110(11): 1465-1473 (2012)). However, recent reports have provided conflicting evidence regarding the potential efficacy of such in situ myocardial regeneration (Qian et al., *Nature*, 485(7400): 593-598 (2012); Song et al., *Nature*, 485(7400): 599-604 (2012); Srivastava et al., *Circ. Res.*, 111(1): 5-8 (2012); Jayawardena et al., *Circ. Res.*, 110(11): 1465-1473 (2012); Protze et al., *J. Mol. Cell. Cardiol.*, 53(3): 323-332 (2012); Chen et al., *Circ. Res.*, 111(1): 50-55 (2012)).

Accordingly, there is a need for additional methods for the treatment and understanding of coronary artery disease, including the generation of iCM cells in situ.

BRIEF SUMMARY OF THE INVENTION

The invention provides materials and methods useful in the treatment and understanding of coronary artery disease. In one aspect, the invention provides a method of treating coronary artery disease by administering vectors encoding one or more angiogenic proteins and one or more cardio-differentiating transcription factors to the heart of a mammal.

The angiogenic protein may be any protein involved in vascularization, e.g., vascular endothelial growth factor (VEGF). The cardio-differentiating transcription factor may be any transcription factor involved in the differentiation of cardiomyocytes, e.g., Gata4, Mef2c, and/or Tbx5.

The vectors may be viral vectors, such as retroviral vectors, lentiviral vectors, human immunodeficiency virus (HIV)-based vectors, herpes simplex virus (HSV)-based vectors, adenovirus-based vectors, parvoviral-based vectors (i.e., adeno-associated virus (AAV)-based vectors), and AAV-adenoviral chimeric vectors. In a preferred embodiment, the method comprises administering an adenoviral vector encoding VEGF and a lentiviral vector encoding Gata4, Mef2c, and Tbx5 (GMT).

BRIEF DESCRIPTION OF THE DRAWINGS

FIGS. 2A-F are a set of photographs and graphs showing iCM generation in vitro. Primary rat dermal fibroblast (RDF) cells were cultured and infected with a GMT lentivirus or a GFP control lentivirus. Fourteen days after infection, cells were fixed and stained for specified cardiomyocyte markers. FIG. 2A is a set of photographs relating to immunofluorescence studies. The first column represents 4',6-diamidino-2-phenylindole (DAPI) staining to identify cell nuclei. The second column represents GFP fluorescence to identify cells infected by at least one of the lentivirus vectors. The third column represents red staining of relevant cardiomyocyte markers (first row: cardiac troponin T (cTnT); second row: myosin heavy chain 7 (MHY7); third row: α sarcomeric actinin). The fourth column depicts a merge of the previous three images. Note the coincidence of these respective markers and binucleated cells typical of cardiomyocyte, and that GFP (−) cells also fail to express markers. Uninfected RDFs did not express either marker (not shown). All photomicropgraphs were taken at 400× magnification (bar=50 μm). FIGS. 2B-F are a set of graphs relating to fluorescence-activated cell sorting (FACS) analysis. Depicted are FACS plots for cTnT staining: RDFs infected with GMT, demonstrating 7% expression of cTnT in GFPP+P cells (FIG. 2B), RDFs infected with GFP control lentivirus (FIG. 2C), uninfected RDFs (FIG. 2D), primary cardiomyocyte control (FIG. 2E), and RDFs infected with GMT, with use of a secondary antibody only (FIG. 2F). The graphs show a minimum of 5,000 events.

FIG. 3 is a graph showing myocardial vascularization. Vascularization of infarct regions is depicted as assessed by determining the number of vessels per microscopic field staining for α-smooth muscle actin in sections obtained 7 wks after coronary ligation and administration of AdVEGF-All6AP+P or the control vector AdNull (n=12/group). * p<0.05.

FIGS. 4A-D are photomicrographs of representative sections of infarct zones from animals treated with AdVEGF-All6AP+P/GMT (top row) or /AdNull/GFP (bottom row) at 100× (left) and 200× (right) magnification, respectively. Bars represent 100 μm. FIG. 4E is a graph of MYH7 cell density as a percent of total sections analyzed (n=6/group). Grade I/II indicates that <50% of the examined microscopic fields were occupied by MYH7P+P cells, and Grade III/IV indicates that >50% of the examined microscopic fields were occupied by MYH7P+P cells (see FIG. 7 for microscopic fields representative of each density grade).

FIG. 5A shows the extent of fibrosis in animals receiving GMT versus GFP control vectors (n=12). * p<0.01. FIG. 5B shows the extent of fibrosis for the four treatment groups (n=6/group). * p<0.05. FIG. 5C shows the number of myofibroblasts identified per microscopic field (200×) in animals receiving GMT versus GFP control vectors (n=12), as identified by staining for α-smooth muscle actin (p=0.09).

FIGS. 6A-C are a set of graphs showing echocardiographic analysis of global ventricular function following in vivo administration of cellular reprogramming and/or AdVEGF-All6AP+P vectors. Echocardiographic studies were performed at the specified time points before and following coronary ligation and administration of AdVEGF-All6AP+P or the control vector AdNull at time 0, and after the administration of lentivirus encoding GMT or a GFP control 3 wks later (n=6). FIG. 6A shows the global ejection fraction for each treatment group. At day 49 (Kruskal-Wallis rank test; p<0.005): AdVEGF-All6AP+P/GMTP Pvs AdNull/GFP: p<0.05; AdVEGF-All6AP+P/GMT versus AdVEGF-All6AP+P/GFP: p<0.05; AdVEGF-All6AP+P/GMT versus AdNull/GMT: p=0.08; AdVEGF-All6AP+P/GFP versus AdNull/GFP: p=0.86). FIG. 6B shows the change in ejection fraction from the time of the lentivirus administration (day 21) baseline to the time of follow up echo 4 wks later (day 49). Top panel: animals receiving GMT versus GFP control vector (n=12). * p<0.01. Bottom panel: each study group analyzed separately (n=6). * p<0.05. AdVEGF-All6AP+P/GMT versus AdVEGF-All6AP+P/GFP: p=0.008; AdVEGF-All6AP+P/GMT versus AdNull/GFP: p<0.001; AdNull/GMT versus AdNull/GFP: p=0.004. FIG. 6C shows left ventricular posterior wall function. Left ventricular posterior wall thickness at end-systole 7 wks following coronary ligation and administration of AdVEGF-All6AP+P or the control vector AdNull (4 wks after the administration of lentivirus encoding GMT or a GFP control). Differences between groups did not reach statistical significance (p=0.09).

FIG. 7 is a set of photographs showing MHY7 cell density classification. MYH7$^+$ cell number was analyzed in a semi-quantitative manner as the MYH7$^+$ cell density in five areas per slide viewed at 200× magnification (at the center of the infarction zone, in the mid areas between the center of infarction and the border zone, and in each border zone adjacent to the infarct). These fields were graded by an investigator blinded to treatment group as follows: (top left) Grade I: <25% of selected microscopic field demonstrating MYH7$^+$ cells; (top right) Grade II: 25%-50% of selected microscopic field demonstrating MYH7$^+$ cells; (bottom left) Grade III: 50%-75% of selected microscopic field demonstrating MYH7$^+$ cells; and (bottom right) Grade IV: >75% of selected microscopic field demonstrating MYH7$^+$ cells.

FIG. 8 is a set of photographs showing infarct vascularization induced by adenoviral mediated transfer of VEGF. Vascularization of infarct regions was assessed by staining for α-smooth muscle actin in sections obtained 7 wks after coronary ligation and administration of AdVEGF-All6AP+P or the control vector AdNull (n=12/group). The photomicrographs show representative sections of infarct zones viewed at 200× after administration of AdNull/GMT (top) or AdVEGF-All6AP+P/GMT (bottom). The bars represent 100 μm.

FIG. 9 is a set of photographs showing myofibroblast density following GMT administration. Myofibroblasts identified by non-vascular α-smooth muscle actin staining of the infarct and border zones of sections of myocardium harvested 7 wks following coronary ligation and administration of AdVEGF-All6AP+P or the control vector AdNull (4 wks after the administration of lentivirus encoding GMT or a GFP control). The photomicrographs show representative sections of infarct zones viewed at 400× after administration of AdNull/GFP (top) or AdVEGF-All6AP+P/GMT (bottom). The bars represent 50 μm.

FIGS. 10A-10B are set of photographs (FIG. 10A) and a graph (FIG. 10B) showing scar vascularization upon administration of AdNull/GFP versus VEGF/GMT. In FIG. 10A, the arrows indicate areas of vascularization. In FIG. 10B, the graphs shows an increased number of vessels/hpf upon administration of VEGF. * p<0.05, α SMA staining.

FIGS. 11A-B are a set of photographs (FIG. 11A) and a graph (FIG. 11B) showing iCM (MHC$^+$) cell density.

DETAILED DESCRIPTION OF THE INVENTION

Figure 1:
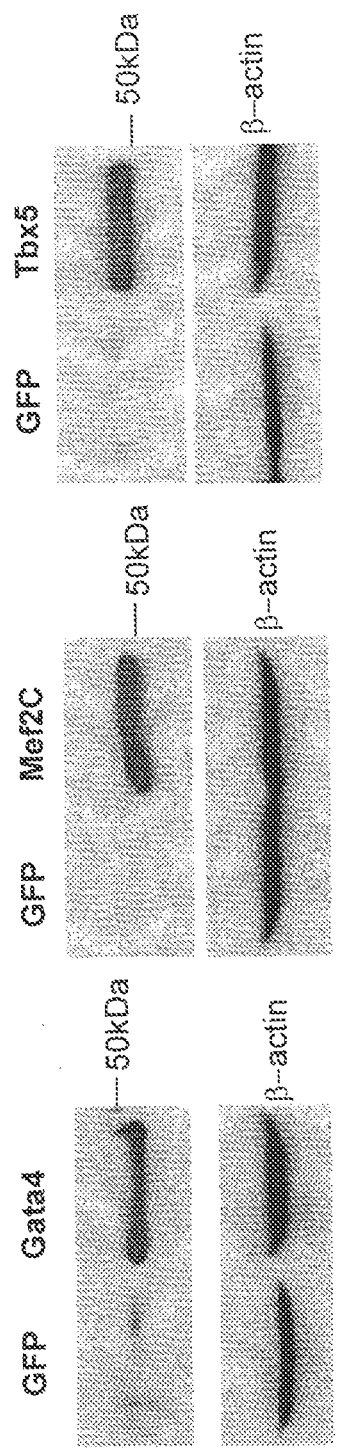
FIG. 1 is a set of photographs showing the generation of lentivirus encoding individual cardiac transcription factors. Lentivirus encoding the transcription factors Gata4, Mef2c, and Tbx5 were prepared in 293T package cells, and protein expression was detected by Western blot analysis using antibodies specific to each transgene. A lentivirus expressing a green fluorescent protein (GFP) marker gene was used as a control for these expression vectors, and beta-actin was used as a loading control.

The invention is based, at least in part, on the concept that, to achieve effective in situ cardio-differentiation, the myocardial scar and surrounding tissue are conditioned with a gene coding for an angiogenic mediator, thereby providing vasculature to a damaged region of the heart that is to be cardio-differentiated by relevant transcription factors. Ischemia may adversely affect the survival and/or function of iCM in an infarct zone, inasmuch as it causes the loss of native cardiomyocytes and exogenous (stem cell) implants (Zhang et al., *J. Mol. Cell. Cardiol.*, 33(5): 907-921 (2001); Reinecke et al., *Circulation*, 100(2): 193-202 (1999); Laflamme et al., *Nature Biotechnol.*, 25(9): 1015-1024 (2007); Retuerto et al., *J. Thorac. Cardiovasc. Surg.*, 127(4): 1041-1049 (2004); Retuerto et al., *J. Thorac. Cardiovasc. Surg.*, 133(2): 478-484 (2007)), such that adequate myocardial scar vascularization can be an important component of an optimized in situ cellular reprogramming strategy (Retuerto et al., *J. Thorac. Cardiovasc. Surg.*, 127(4): 1041-1049 (2004); Retuerto et al., *J. Thorac. Cardiovasc. Surg.*, 133(2): 478-484 (2007)). The use of angiogenic conditioning markedly improves the effectiveness of the use of cardio-differentiating factors to improve cardiac function after myocardial infarction or other coronary artery disease.

The invention provides a method of treating coronary artery disease in a mammal, comprising administering to the heart of the mammal a first vector encoding one or more angiogenic proteins which induce vascularization in the heart of the mammal, and a second vector encoding one or more cardio-differentiating transcription factors which induce the production of induced cardiomyocytes (iCM) in the heart of the mammal, whereby the coronary artery disease in the mammal is treated. Desirably, the first and second vectors are administered to the same region of the heart.

The term "coronary artery disease" refers to any disorder or condition involving the coronary arteries. Coronary artery disease is usually attributable to the deposition of atheromatous plaque on the arterial walls. Narrowing or occlusion of the arterial lumen results in reduced delivery of oxygen and nutrients to the heart. Although arterial occlusion usually progresses slowly, sudden blockage of an artery by a thrombus or embolus is also possible. Manifestations of coronary artery disease include angina, ischemia, myocardial infarction, cardiomyopathy, congestive heart failure, arrhythmias, and aneurysm formation.

The term "region of the heart" refers to any region of the heart affected by coronary artery disease. The region of the heart may include the atria, ventricles, and/or vessels of the heart. The region of the heart may also be a region damaged, for example, by myocardial infarction. In this respect, the region of the heart may be a myocardial scar or peri-infarcted region of the heart.

The term "mammal" refers to any suitable mammal, including, but not limited to, a mouse, rat, cat, dog, guinea pig, hamster, rabbit, cat, dog, pig, cow, horse, primate, and human. The mammal typically is a human.

The term "angiogenic protein" refers to a protein that is involved in vascularization. For example, the angiogenic protein may be one or more of VEGF (vascular endothelial growth factor) (e.g., VEGF-A (120, 164, and 188), VEGF-B, VEGF-C, or VEGF-D, VEGF-E, VEGF-F), FGF (fibroblast growth factor) (e.g., FGF-1, FGF-2, FGF-3, FGF-4, FGF-5, FGF-6, FGF-7, FGF-8, FGF-9, FGF-10, FGF-11, FGF-12, FGF-13, FGF-14, FGF-15, FGF-16, FGF-17, FGF-18, FGF-19, FGF-20, FGF-21, FGF-22, or FGF-23), PGF (placental growth factor), NRP-1 (neuropilin-1), ANG (angiopoietin) (e.g., ANG-1 or ANG-2), PDGF (platelet-derived growth factor) (e.g., PDGF-AA, PDGF-BB, or PDGF-AB), TGF-β (transforming growth factor beta) (e.g., TGF-β1, TGF-β2, or TGF-β3), MCP-1 (monocyte chemotactic protein-1), VE-cadherin (vascular endothelial cadherin), ephrin, plasminogen activator or plasminogen activator inhibitor, eNOS (endothelial nitric oxide synthase), COX-2 (cyclooxygenase-2), CD133, MMP (matrix metalloproteinase), and DLL44 (delta-like ligand 4). The angiogenic protein may also be a receptor for any of the aforementioned angiogenic proteins. In a preferred embodiment, the angiogenic protein is VEGF.

The term "cardio-differentiating transcription factor" refers to a protein, agent, or transcription factor that is involved in the induction of cardio-differentiation or the production of iCM, e.g., the production of iCM from myocardial fibroblasts. For example, the cardio-differentiating transcription factor may be one or more of Hopx (homeodomain-only protein), Nkx2-5 (homeobox protein Nkx-2.5), Hrt2 (Hairy-related transcription factor 2), Pitx2 (paired-like homeodomain transcription factor 2 or pituitary homeobox 2), Smyd1 (MYND-domain-containing protein 1), Myocd (myocardin), Baf60c (BRG1/Brm-associated factor of 60 kDa, subunit c), Tbx5 (T-box transcription factor 5), Srf (serum response factor), Gata4 (globin transcription factor 4), Isl1 (insulin gene enhancer protein 1), Mef2c (myocyte-specific enhancer factor 2C or MADS box transcription enhancer factor 2, polypeptide C), Hand2 (heart- and neural crest derivatives-expressed protein 2), and Mesp1 (mesoderm posterior 1 homolog). The cardio-differentiating transcription factor may also be a receptor for any of the aforementioned cardio-differentiating transcription factors. In a preferred embodiment, the cardio-differentiating transcription factors are the combination of Gata4, Mef2c, and Tbx5 (GMT).

The term "vector" refers to any vehicle used to transfer genetic material to a target cell. The invention provides a vector comprising a nucleic acid sequence encoding one or more angiogenic proteins and a vector comprising a nucleic acid sequence encoding one or more cardio-differentiating transcription factors. The vectors may be non-viral vectors, including, for example, lipoplexes, polyplexes, dendrimers, and nanoparticles. Preferably, the vectors may be viral vectors, including, for example, retroviral vectors, lentiviral vectors, human immunodeficiency virus (HIV)-based vectors, herpes simplex virus (HSV)-based vectors, adenovirus-based vectors, parvoviral-based vectors (i.e., adeno-associated virus (AAV)-based vectors), and AAV-adenoviral chimeric vectors. These gene transfer vectors can be prepared using standard recombinant DNA techniques described in, e.g., Sambrook et al., *Molecular Cloning, a Laboratory Manual*, 2d edition, Cold Spring Harbor Press, Cold Spring Harbor, N.Y. (1989), and Ausubel et al., *Current Protocols in Molecular Biology*, Greene Publishing Associates and John Wiley & Sons, New York, N.Y. (1994).

Retrovirus is an RNA virus capable of infecting a wide variety of host cells. Upon infection, the retroviral genome integrates into the genome of its host cell and is replicated along with host cell DNA, thereby constantly producing viral RNA and any nucleic acid sequence incorporated into the retroviral genome. When employing pathogenic retroviruses, e.g., human immunodeficiency virus (HIV) or human T-cell lymphotrophic viruses (HTLV), care must be taken in altering the viral genomic to eliminate toxicity. A retroviral vector can additionally be manipulated to render the virus replication-incompetent. As such, retroviral vectors are considered to be particularly useful for stable gene transfer in vivo.

Lentiviral vectors, such as HIV-based vectors, are exemplary of retroviral vectors used for gene delivery. Unlike other retroviruses, lentiviral vectors are known to incorporate their passenger genes into non-dividing cells, making lentiviral vectors particularly useful in gene therapy. Lentiviruses are composed of two copies of RNA, a nuclear capsid (NC), a capsid (CA), a membrane associated matrix (MA), envelope proteins such as surface glycoproteins (SU) and transmembrane proteins (TM), and enzymes such as integrase (IN), protease (PR), and reverse transcriptase (RT), and accessory proteins. Lentiviral vectors rely on the physical separation into different plasmids of proteins required for viral particle formation and infectivity (the packaging and the envelope constructs) and of cis-acting sequences sufficient to mobilize the viral genome (the transfer vector). The latter constitutes the core of the vector, which is a mini-viral genome devoid of viral open reading frames (ORFs), but carrying an expression cassette for the transgene of interest. As a consequence of the deletion of viral ORFs from the transfer vector, virions can undergo a single round of infection at the conclusion of which proviral DNA expresses only the transgene of interest (Durand et al., Viruses, 3(2): 132-159 (2011)).

HSV-based viral vectors are suitable for use as a gene transfer vector to introduce nucleic acids into neurons or other tissues. The mature HSV virion consists of an enveloped icosahedral capsid with a viral genome consisting of a linear double-stranded DNA molecule that is 152 kb. Most replication-deficient HSV vectors contain a deletion to remove one or more intermediate-early genes to prevent replication. Advantages of the herpes vector are its ability to enter a latent stage that can result in long-term DNA expression and its large viral DNA genome that can accommodate exogenous DNA up to 25 kb.

Adenovirus (Ad) is a 36 kb double-stranded DNA virus that efficiently transfers DNA in vivo to a variety of different target cell types. For use in the inventive methods, the virus is preferably made replication deficient by deleting select genes required for viral replication, such as, for example, all or portions of the E1, E2, and/or E4 regions. The expendable E3 region is also frequently deleted to allow additional room for a larger DNA insert. The vector can be produced in high titers and can efficiently transfer DNA to replicating and non-replicating cells. The newly transferred genetic information remains epi-chromosomal, thus eliminating the risks of random insertional mutagenesis and permanent alteration of the genotype of the target cell. Adenoviral vectors can be derived from any serotype of adenovirus. Adenoviral stocks that can be employed as a source of adenovirus can be amplified from adenoviral serotypes 1 through 51, which are currently available from the American Type Culture Collection (ATCC, Manassas, Va.), or from any other serotype of adenovirus available from any other source. For instance, an adenovirus can be of subgroup A (e.g., serotypes 12, 18, and 31), subgroup B (e.g., serotypes 3, 7, 11, 14, 16, 21, 34, and 35), subgroup C (e.g., serotypes 1, 2, 5, and 6), subgroup D (e.g., serotypes 8, 9, 10, 13, 15, 17, 19, 20, 22-30, 32, 33, 36-39, and 42-47), subgroup E (serotype 4), subgroup F (serotypes 40 and 41), or any other adenoviral serotype. Preferably, however, an adenovirus is of serotype 2, 5, or 9. In one embodiment, the adenoviral vector is of serotype 5 and has deletions in the E1 and E3 regions.

AAV vectors are viral vectors of particular interest for use in gene therapy protocols (see, e.g., Santos Coura et al., Virology J., 4: 99 (2007)). AAV is a nonenveloped DNA virus, which is not known to cause human disease. AAV usually requires co-infection with a helper virus (i.e., an adenovirus or a herpes virus), or expression of helper genes, for efficient replication. In the absence of a helper virus, AAVs establish a latent infection within the target cell. The genome of AAV consists of an approximately 4.7 kb single-stranded linear DNA that contains two open reading frames (ORFs). The left ORF encodes nonstructural Rep proteins, and the right ORF encodes capsid (Cap) proteins VP1, VP2, and VP3. Each end of the AAV genome comprises a 145 base inverted terminal repeat (ITR), which contains the viral origin of DNA replication and the packaging signal. AAV ITR nucleotide sequences have been previously described, (see, e.g., Kotin et al., Human Gene Ther., 5: 793-801 (1994); Berns "Parvoviridae and Their Replication" in Fundamental Virology, 2nd Edition (B. N. Fields and D. M. Knipe, eds.)).

AAV vectors used for administration of a therapeutic nucleic acid can have approximately 96% or more of the parental genome deleted, such that only the ITRs remain. This eliminates immunologic or toxic side effects due to expression of viral genes. In addition, delivering the AAV Rep protein enables integration of the AAV vector comprising AAV ITRs into a specific region of genome, if desired. Host cells comprising an integrated AAV genome show no change in cell growth or morphology (see, for example, U.S. Pat. No. 4,797,368). AAV vectors can be derived from any serotype of AAV, including, but not limited to, any of the 11 known AAV serotypes (i.e., AAV1, AAV2, AAV3, AAV4, AAV5, AAV6, AAV7, AAV8, AAV9, AAV10, and AAV11). AAV stocks that can be employed as a source of AAV can be amplified from AAV1, AAV2, AAV3, AAV4, or AAV5, which are currently available from the American Type Culture Collection (ATCC, Manassas, Va.), or from any other serotype of AAV available from any other source. Serotype 2 AAV (AAV2) has been the most extensively studied of all of the AAV serotypes. AAV2 can infect many different cell types, including skeletal muscle cells, neurons, vascular smooth muscle cells, and hepatocytes. In the context of the invention, an AAV2 gene transfer vector preferably is used to infect neurons.

The nonpathogenic and persistent long-term nature of AAV infection, combined with its wide range of infectivity, has made this virus an important candidate as a therapeutic gene transfer vector. However, if desired, the integrative properties of AAV can be conferred to adenovirus by constructing an AAV-Ad chimeric vector. For example, the AAV ITRs and nucleic acid encoding the Rep protein incorporated into an adenoviral vector enable the adenoviral vector to integrate into a mammalian cell genome.

Regulatory sequences for use in the vector of the invention can be provided from commonly used promoters derived from viruses such as polyoma, adenovirus 2, cytomegalovirus, and simian virus 40. The use of viral regulatory elements to direct expression of the protein can allow for high level constitutive expression of the protein in a variety of host cells. Ubiquitously expressing promoters also can be used, including, for example, the early cytomegalovirus promoter (see, e.g., Boshart et al., *Cell*, 41: 521-530 (1985)), herpesvirus thymidine kinase (HSV-TK) promoter (see, e.g., McKnight et al., *Cell*, 37: 253-262 (1984)), β-actin promoters (e.g., the human β-actin promoter as described by Ng et al., *Mol. Cell Biol.*, 5: 2720-2732 (1985)), and colony stimulating factor-1 (CSF-1) promoter (see, e.g., Ladner et al., *EMBO J.*, 6: 2693-2698 (1987)).

Alternatively, the regulatory sequences of the vector can direct expression of the gene preferentially in a particular cell type, i.e., tissue-specific regulatory elements can be used. Examples of tissue-specific promoters which can be used include cardiovascular system specific promoters, i.e., promoters that are (a) essentially inactive outside the cardiovascular system or (b) more active in the cardiovascular system than in other systems. For example, the tissue-specific promoter may be a promoter specific for the heart or blood vessels. The promoter can be specific for particular cell types, such as fibroblasts, cardiomyocytes, or endothelial cells.

In order to produce recombinant viral particles, a viral vector can be introduced into a suitable host cell using known techniques, such as by transfection. A number of transfection techniques are generally known in the art (see, e.g., Graham et al., *Virology*, 52: 456-467 (1973); Sambrook et al., *Molecular Cloning, a Laboratory Manual*, 2d edition, Cold Spring Harbor Press, Cold Spring Harbor, N.Y. (1989); Davis et al., *Basic Methods in Molecular Biology*, Elsevier (1986); and Chu et al., *Gene*, 13: 97 (1981)). Particularly suitable transfection methods include calcium phosphate co precipitation (see, e.g., Graham et al., *Virology*, 52: 456-467 (1973)), direct micro injection into cultured cells (see, e.g., Capecchi, *Cell*, 22: 479 488 (1980)), electroporation (see, e.g., Shigekawa et al., *BioTechniques*, 6: 742-751 (1988)), liposome mediated gene transfer (see, e.g., Mannino et al., *BioTechniques*, 6: 682-690 (1988)), lipid mediated transduction (see, e.g., Felgner et al., *Proc. Natl. Acad. Sci.* (USA), 84: 7413-7417 (1987)), and nucleic acid delivery using high velocity microprojectiles (see, e.g., Klein et al., *Nature*, 327: 70-73 (1987)).

Suitable host cells for producing recombinant viral particles include, but are not limited to, microorganisms, yeast cells, insect cells, and mammalian cells, that can be, or have been, used as recipients of an exogenous nucleic acid molecule. Thus, a "host cell" as used herein generally refers to a cell which has been transfected with an exogenous nucleic acid molecule. The host cell includes any eukaryotic cell or cell line so long as the cell or cell line is not incompatible with the protein to be expressed, the selection system chosen, or the fermentation system employed. Non-limiting examples include CHO dhfr-cells (see, e.g., Urlaub et al., *Proc. Natl. Acad. Sci.* (USA), 77: 4216-4220 (1980)), 293 cells (see, e.g., Graham et al., *J. Gen. Virol.*, 36: 59 (1977)), and myeloma cells such as SP2 and NS0 (see, e.g., Galfre et al., *Meth. Enzymol.*, 73: 3-46 (1981)).

In one embodiment, the stable human embryonic kidney cell line 293 (e.g., ATCC Accession No. ATCC CRL1573) is used in the practice of the invention. The 293 cell line is readily transfected and provides a particularly convenient platform in which to produce recombinant virions. For example, to produce recombinant lentiviral particles, a human 293 cell line may be co-transfected with a lentiviral vector containing the transgene, a packaging vector (e.g., psPAX), and an envelope vector (e.g., pMD2G).

The first and second vectors may each be derived from the same virus, e.g., the first vector may be an adenoviral vector and the second vector may be an adenoviral vector. Alternatively, the first and second vectors may each be derived from different viruses, e.g., the first vector may be an adenoviral vector and the second vector may be a lentiviral vector. In an alternative embodiment, a single vector encodes both the one or more angiogenic proteins and the one or more cardio-differentiating transcription factors, i.e., the first and second vector are the same (single) vector.

When the first and second vectors are two vectors, the first and second vectors may be administered in any order. For instance, the first vector may be administered before, after, or at the same time as the second vector. The first vector may be administered, e.g., about 1 hour, 1 day, 3 days, 5 days, 1 week, 2 weeks, 3 weeks, 4 weeks, 5 weeks, 6 weeks, 7 weeks, 8 weeks, 9 weeks, or 10 weeks before or after the second vector. In a preferred embodiment, the first vector is administered about 3 weeks before the second vector.

The administration of a lentiviral vector encoding three transcription factors (Gata4, Mef2c and Tbx5 (GMT)) used as a stimulus for iCM generation together with administration of an adenoviral vector encoding all three major isoforms of VEGF results in greater improvements in post-infarct myocardial function than does the administration of GMT or VEGF alone. In fact, this discovery stands in contradistinction to the recent work of other investigators that suggests that cellular reprogramming mediated by GMT strategy is ineffectual (Chen et al., *Circ. Res.*, 111(1): 50-55 (2012)).

The coronary artery disease of the mammal may be considered to be treated if any improvement in cardiac function or pathophysiology results from the administration of the vectors. For example, increased numbers of cardiomyocytes or iCM, reduced fibrosis, increased vascularization, improved ventricular function, and increased ejection fraction are indicators of successful treatment of coronary artery disease. These indicators may be measured or evaluated by any method known in the art, including immunohistochemistry, immunofluorescence, fluorescence activated cell sorting (FACS), microscopy, or echocardiography.

The presumptive origin of improvements in post-infarct ventricular function is the generation of functional iCM in areas of myocardial scar and the enhancement of the survival and/or function of these "reprogrammed" myocytes by scar prevascularization (Qian et al., *Nature*, 485(7400): 593-598 (2012); Passier et al., *Cell Stem Cell*, 7(2): 139-141 (2010); Song et al., *Nature*, 485(7400): 599-604 (2012); Srivastava et al., *Circ. Res.*, 111(1): 5-8 (2012); Retuerto et al., *J. Thorac. Cardiovasc. Surg.*, 127(4): 1041-1049 (2004); Retuerto et al., *J. Thorac. Cardiovasc. Surg.*, 133(2): 478-484 (2007)). Interestingly, the observed improvements in ejection fraction and decreases in fibrosis following cellular reprogramming appear to far exceed what would be expected solely on the basis of the relatively inefficient generation of iCM from substrate cells (Qian et al., *Nature*, 485(7400): 593-598 (2012); Passier et al., *Cell Stem Cell*, 7(2): 139-141 (2010); Song et al., *Nature*, 485(7400): 599-604 (2012); Srivastava et al., *Circ. Res.*, 111(1): 5-8 (2012)). More specifically, in comparison to a rate of transdifferentiating infarct fibroblasts into iCM in vivo in the range of 1%-20%, reductions in fibrosis and improvements in ejection fraction ranging up to 50% suggest alternative or additional mechanisms may be responsible for these outcomes (Qian et al., *Nature*, 485(7400): 593-598 (2012); Song et al., *Nature*, 485(7400): 599-604 (2012); Jayawardena et al., *Circ. Res.*, 110(11): 1465-1473 (2012)).

The generation of functionally competent, contractile iCM may individually contribute to the restoration of global cardiac function. The significant increases in MYH7$^+$ (cardiomyocyte) cell density in GMT treated versus control animals in both infarct and border zones, similar to the previous observations of Qian et al. and Song et al., is supportive of this mechanism (Qian et al., Nature, 485 (7400): 593-598 (2012); Song et al., Nature, 485(7400): 599-604 (2012)). Alternatively, the generation of iCM in thinned zones of infarction might improve wall stresses and thereby decrease global myocardial workloads, as supported by observations of the improved systolic function of remote left ventricular wall segments in treated animals, and as previously postulated to be a mechanism of action underlying the efficacy of stem cell implant therapies (Leor et al., Circulation, 94(Suppl. 9): 11332-11336 (1996); Taylor et al., Nature Med., 4(8): 929-933 (1998); Tomita et al., Circulation, 100(Suppl. 19): 11247-11256 (1999); Orlic et al., Nature, 410(6829): 701-704 (Apr. 5, 2001); Scorsin et al., J. Thorac. Cardiovasc. Surg., 119(6): 1169-1175 (2000); Hare et al., Curr. Opin. Organ Transplant, 13(5): 536-542 (2008); Rosenzweig, N. Engl. J. Med., 355(12): 1274-1277 (2006); Murry et al., J. Am. Coll. Cardiol., 47(19): 1777-85 (2006); Menasche, J. Mol. Cell. Cardiol., 50(2): 258-265 (2010); Min et al., J. Appl. Phys., 92(1): 288-296 (2002)).

The dramatic decrease in fibrosis seen in animals treated according to the method of the present invention appears to far exceed increases in the number of newly generated iCM, thereby suggesting that the decrease in fibrosis may also contribute to the significant improvements in ejection fraction observed in treated animals. It is conceivable that a paracrine effect of a relatively limited number of iCM might underlie this reduction in fibrosis, due to the expression by iCM of chemokines such as basic fibroblast growth factor and tissue inhibitor of matrix metalloproteinase (TIMP)-2 that have been reported to limit or reduce fibrosis (Daskalopoulos et al., Microsc. Microanal., 18(1): 35-49 (2012); Fedak et al., Circ. Heart Failure, 5(3): 349-356 (2012); van den Borne et al., Nature Rev. Cardiol., 7(1): 30-37 (2010)).

Alternatively, the administration of cellular reprogramming and/or VEGF transgenes may divert resident/scar fibroblasts away from their normal post-infarct differentiation into myofibroblasts, which are known to produce fibrosis via expression of collagen and other extracellular matrix components, and towards a more benign fate as iCM (Daskalopoulos et al., Microsc. Microanal., 18(1): 35-49 (2012); Fedak et al., Circ. Heart Failure, 5(3): 349-356 (2012); van den Borne et al., Nature Rev. Cardiol., 7(1): 30-37 (2010); Chen et al., Am. J. Physiol. Heart Circ. Physiol., 291(4): H1653-1658 (2006); Yang et al., J. Appl. Physiol., 93(3): 1140-1151 (2002); Zhang et al., Circulation, 119(13): 1776-1784 (2009); Song et al., Biochem. Biophys. Res. Comm., 354(4): 999-1003 (2007); Claes et al., Cardiovasc. Res., 91(3): 369-370 (2011)). The four-fold reduction of myofibroblast populations observed in GMT-treated animals versus controls, consistent with a similar trend in reduced extent of fibrosis, supports this supposition. Theoretically, alternative processes such as myofibroblast apoptosis and/or repressed function (i.e., decreased extracellular matrix component expression) could also play a role in such mechanisms (Daskalopoulos et al., Microsc. Microanal., 18(1): 35-49 (2012); Fedak et al., Circ. Heart Failure, 5(3): 349-356 (2012); van den Borne et al., Nature Rev. Cardiol., 7(1): 30-37 (2010); Chen et al., Am. J. Physiol. Heart Circ. Physiol., 291(4): H1653-1658 (2006); Yang et al., J. Appl. Physiol., 93(3): 1140-1151 (2002); Zhang et al., Circulation, 119(13): 1776-1784 (2009); Song et al., Biochem. Biophys. Res. Comm., 354(4): 999-1003 (2007); Claes et al., Cardiovasc. Res., 91(3): 369-370 (2011)).

The use of lentivirus and adenovirus vectors which infect dividing and non-dividing cells (including cardiomyocytes) raises the possibility also of GMT/VEGF effects on resident cardiomyocytes in addition to the targeting of fibroblasts (Qian et al., Nature, 485(7400): 593-598 (2012); Passier et al., Cell Stem Cell, 7(2): 139-141 (2010); Song et al., Nature, 485(7400): 599-604 (2012); Srivastava et al., Circ. Res., 111(1): 5-8 (2012); Jayawardena et al., Circ. Res., 110(11): 1465-1473 (2012)). Some evidence in the literature suggests that such effects might include changes in cardiomyocyte structure, function, or stability/resistance to ischemia (i.e., cardiac "super cells") (Daskalopoulos et al., Microsc. Microanal., 18(1): 35-49 (2012); Fedak et al., Circ. Heart Failure, 5(3): 349-356 (2012); van den Borne et al., Nature Rev. Cardiol., 7(1): 30-37 (2010); Chen et al., Am. J. Physiol. Heart Circ. Physiol., 291(4): H1653-1658 (2006); Yang et al., J. Appl. Physiol., 93(3): 1140-1151 (2002); Zhang et al., Circulation, 119(13): 1776-1784 (2009); Song et al., Biochem. Biophys. Res. Comm., 354(4): 999-1003 (2007); Claes et al., Cardiovasc. Res., 91(3): 369-370 (2011)). GMT and/or VEGF when administered via these vectors might influence the differentiation of other non-proliferating cells, such as resident cardiac progenitor cells, fibroblasts, or endocardial cells towards a cardiomyocyte fate and/or away from a myofibroblast phenotype.

Scar vascularization is important to support the survival and function of stem cell implants, and a plateau in neovascularization begins 3 weeks following administration of VEGF (Retuerto et al., J. Thorac. Cardiovasc. Surg., 127(4): 1041-1049 (2004); Retuerto et al., J. Thorac. Cardiovasc. Surg., 133(2): 478-484 (2007); Amano et al., Mol Ther., 12(4): 716-724 (2005)). Preliminary cell survival studies suggest that similar considerations apply to observation of increased neovascularization providing the nutrient perfusion needed to support the conversion of low metabolic fibroblasts into high metabolic (induced) cardiomyocytes.

The importance of scar prevascularization to the presently described in situ cellular reprogramming strategy is supported by the observation of the ability of AdVEGF to induce scar vascularization in an acute myocardial infarction model, together with the observation of significant improvements in ejection fraction when VEGF is administered as a supplement to GMT. The lack of change in MYH7$^+$ cell density observed when VEGF is administered without GMT suggests that VEGF does not play a significant, independent role in cellular reprogramming in this setting. In contrast, in the context of the lag in neovascularization induced by VEGF relative to the more rapid time course of myocardial infarction, and the observation of an equivalent extent of fibrosis in animals treated with VEGF versus without VEGF, the (comparatively limited) improvement in ejection fraction observed after VEGF administration (without GMT) is potentially attributable to the anti-apoptotic as well as the angiogenic properties of VEGF, in promoting the viability and/or function of border zone cells (Daskalopoulos et al., Microsc. Microanal., 18(1): 35-49 (2012); Fedak et al., Circ. Heart Failure, 5(3): 349-356 (2012); van den Borne et al., Nature Rev. Cardiol., 7(1): 30-37 (2010); Chen et al., Am. J. Physiol. Heart Circ. Physiol., 291(4): H1653-1658 (2006); Yang et al., J. Appl. Physiol., 93(3): 1140-1151 (2002); Zhang et al., Circulation, 119(13): 1776-1784 (2009); Song et al., Biochem. Biophys. Res. Comm., 354(4): 999-1003 (2007); Claes et al., Cardiovasc. Res., 91(3): 369-370 (2011)).

The methods of the invention may be combined with any other known treatments for coronary artery disease, such as pharmacological therapies or interventional/surgical procedures. Pharmacological therapies include anti-platelet and anticoagulant drugs, beta blockers, ACE inhibitors, nitrates, and calcium channel blockers. Interventional procedures and surgeries include coronary artery bypass grafting (commonly called bypass or CABG), which is usually reserved for patients with severe coronary artery disease, and percutaneous coronary intervention (commonly called angioplasty or PCI), which typically involves involving coronary artery stent placement.

The following example further illustrates the invention but, of course, should not be construed as in any way limiting its scope.

Example 1

This example demonstrates the administration of adenovirus-mediated VEGF into infarcted myocardium following lentivirus-mediated administration of the cellular reprogramming transcription factors Gata 4, Mef2c and Tbx5 (GMT).

Vectors and Cells:

An adenovirus vector (AdVEGF-All6A$^+$) based on an Ad5 serotype backbone with deletions in the E1 and E3 regions and containing an artificial splice sequence cassette was used to provide delivery of all three major isoforms of VEGF (121, 165, and 189) (Amano et al., Mol Ther., 12(4): 716-724 (2005)). An analogous construct with an empty expression cassette (AdNull) was used as a control vector.

Lentivirus vectors were constructed to provide expression of Gata4, Mef2c, and Tbx5 (GMT) in targeted myocardial tissues. For GMT vector construction, RNA was first isolated from rat heart using TRIzol reagent (Invitrogen) and converted to cDNA using a reverse transcription kit (Roche). These samples (for Mef2c) or commercially available cDNA (for Gata4 and Tbx5; AddGene) were used to amplify relevant coding sequences using primers based on the PubMed nucleotide coding sequences for these three transgenes (Table 1) (Ieda et al., Cell, 142(3): 375-386 (2010); Qian et al., Nature, 485(7400): 593-598 (2012)). Primers were designed to include a SaI1 binding site 5' and Xho1 restriction site 3' of each coding sequence. Gene inserts were amplified using a PCR kits (Roche) and cloned into the pENTR3C vector prior to homologous recombination into the F12-CMV vector (Invitrogen) under the control of a CMV promoter. F12-CMV also includes an eGFP cassette under the control of an ubiquitin promoter for lineage and efficiency analysis.

TABLE 1

Primers used for plasmid construction

| Primer Name | Sequence | Tm |
|---|---|---|
| Gata4 5' | GGCGGTCGACATGTACCA AAGCCTGGCTATG (SEQ ID NO: 1) | 72.6 |
| Gata4 3' | GATTCTCGAGTACGCGGT GATTATGTCCCCATG (SEQ ID NO: 2) | 70.9 |
| Mef2c 5' | GGACTGTCGACATGGGGA GAAAAAGATTCAG (SEQ ID NO: 3) | 68.5 |
| Mef2c 3' | TGTGACTCGAGTCATGTT GCCCATCCTTCAGAGAG (SEQ ID NO: 4) | 71.7 |
| Tbx5 5' | CACCGTCGACATGGCCGA CGCAGATGAG (SEQ ID NO: 5) | 73.4 |
| Tbx5 3' | CCTTCTCGAGTCAAGCTA TTCTCGCTCCACTCTG (SEQ ID NO: 6) | 71.9 |

Gata4, Mef2c, and Tbx5 F12-CMV plasmids thus generated were transfected into the 293T human kidney fibroblasts cell line (ATCC) along with gateway system using plasmids pMD2G and psPAX via LIPOFETAMINE™ 2000 reagent (Invitrogen). Viral bearing supernatant was isolated and cellular debris was removed by centrifugation and syringe filtering (0.45 μm pore size; Sarstedt). Virus was further concentrated by centrifugation (2 h at 10,000×g) and supernatants were then aspirated and pellets diluted in viral diluent (3% sucrose, 10 mM Tris-HCl, pH 7.6, 150 mM NaCl).

Dermal fibroblasts derived from 1 cm$^2$ biopsies of the abdominal skin of Fischer 344 rats were plated on plastic dishes (Xu et al., Proc. Natl. Acad. Sci. (USA), 106(3): 808-813 (2009); Ieda et al., Cell, 142(3): 375-386 (2010)). Attached fibroblasts were cultured for 7 d in DMEM medium/10% FBS at 10$^4$/cm$^2$. Cells were then re-plated and infected with appropriate vectors after 24 h. Cardiomyocytes were obtained from the neonatal ventricles of Sprague Dawley rats (gift of E. Entcheva) which were cut into small pieces and digested with collagenase type II solution. A single-cell suspension of primary cardiomyocytes was then obtained by gentle passage through a 40-μm cell strainer and cells were plated on tissue culture treated dishes (Thermo Scientific).

In Vitro Immunofluorescence (IF) Studies:

Lentivirus encoding GMT or GFP control vectors in the presence of 8 μg/ml POLYBRENE™ (Millipore) were added to rat dermal fibroblast culture media (DMEM+10% FBS) for 16 hrs. This media was then removed and the cells were allowed to transdifferentiate under normal culture conditions over a 14 d time course. These cells were washed twice with phosphate buffered saline (PBS) and fixed with 4% paraformaldehyde (Affymetrix) for 10 min. Cells were then permeabilized with 0.5% saponin (Sigma) at room temperature for 10 min. Slides were blocked with 10% goat serum (Santa Cruz) prior to incubation in 5% goat serum with primary antibodies directed toward cardiac troponin T (cTnT; Abcam), beta myosin heavy chain 7 (MYH7; Sigma), or a sarcomeric actinin (Sigma). Primary antibodies were bound with fluorescent secondary (647 nm; Alexafluor), and fluorescence was visualized using a Ti—S inverted phase/fluorescent microscope with SPOT cooled 2.0 megapixel digital camera system (Nikon).

Fluorescence Activated Cell Sorting (FACS):

For FACS analyses, cells were washed with PBS and treated with 0.05% trypsin (Gibco). These cells were then pelleted and permeabilized with 0.1% saponin for 30 min at 4° C., re-pelleted and suspended in 5% goat serum, and incubated with relevant primary antibodies followed by incubation with a fluorescent secondary antibody (647 nm; Alexafluor). Cells were fixed with 1% paraformaldehyde and analyzed for fluorescence using Cell Quest V3.3 software on a FACS Calibur Flow Cytometer (Becton/Dickinson) (Ieda et al., *Cell*, 142(3): 375-386 (2010); Efe et al., *Nature Cell. Bio.*, 13(3): 215-222 (2011); Qian et al., *Nature*, 485(7400): 593-598 (2012)).

Myocardial Infarction in an Animal Model:

Myocardial infarction was created by coronary ligation, as previously described, in adult male Fischer 344 rats (275-300 g; Harlan; Indianapolis, Ind.), using protocols approved by the State University of New York, Stony Brook Institutional Animal Care and Use Committee (IACUC) (Retuerto et al., *J. Thorac. Cardiovasc. Surg.*, 127(4): 1041-1049 (2004); Retuerto et al., *J. Thorac. Cardiovasc. Surg.*, 133(2): 478-484 (2007)). Animals were housed, operated on, and cared for in facilities run by the Division of Laboratory Animal Resources (DLAR) at Stony Brook University, which is fully accredited by the Association for the Assessment and Accreditation of Laboratory Animal Care (AAALAC) International.

Animals were first anesthetized with isofluorane 4% in an induction box, intubated, and placed on a rodent ventilator (Harvard Apparatus) using isofluorane inhalation (3.5%) supplemented with oxygen. Lidocaine (4 mg/kg) was administered intramuscularly. A left thoracotomy was then performed, and the left coronary artery was ligated 1 to 2 mm from its origin with a 7-0 polypropylene suture. This prep consistently produces a gross (pale) antero-apical myocardial infarction (MI) with <20% mortality.

At the time of coronary ligation, five uniformly distributed 20 µL injections each containing $2 \times 10^8$ pu ($1 \times 10^9$ total dose) of Ad VEGF-All6A$^+$ or AdNull (n=12/group) was administered around the infarct zone, identified as an area of blanching on the anterolateral wall of the left ventricle, by operators blinded to treatment group. The chest was then sutured closed layer-by-layer, and the animals were placed in a heated chamber and allowed to recover under supervision. Ketorolac (3-5 mg/kg) and buprenorphine (0.05-0.1 mg/kg) were administered subcutaneously at the time of closure and every 12-24 hr post-operatively as needed, determined by the level of activity displayed by the animals.

A second thoracotomy was performed 3 wks later, and animals previously receiving AdVEGF-All6A$^+$ or AdNull each then underwent administration into the infarct zone of $1 \times 10^5$ TU of lentivirus (5 uniformly distributed 20 µL injections) encoding Gata4, Mef2c, or Tbx5 coupled to a GFP marker, or encoding GFP alone (final n=6/group). Animals again recovered as described above. Euthanasia was later achieved 4 wks later by deep (4%) isoflurane anesthesia followed by exsanguination, consistent with AVMA guidelines.

Echocardiography:

Echocardiography was performed under light anesthesia with 3% isoflurane using a Veno 770™ Imaging System (VisualSonics Inc., Toronto, ON, Canada) at five different time points: prior to and 3 d after coronary ligation and AdVEGF-All6A$^+$ or AdNull, at the time of GMT or GFP administration 21 d later (baseline), and then 2 wks and 4 wks later after baseline (post-ligation day 35 and day 49, respectively) (Retuerto et al., *J. Thorac. Cardiovasc. Surg.*, 127(4): 1041-1049 (2004); Retuerto et al., *J. Thorac. Cardiovasc. Surg.*, 133(2): 478-484 (2007)). Echo images were obtained of the left ventricle in both parasternal long-axis and short-axis views by investigators blinded to treatment group. Left ventricular end-systolic and end-diastolic diameters and left ventricular septal and posterior thickness (in both end-systolic and end-diastolic phases) were measured from M-mode tracings. These imaging data were then analyzed by investigators blinded to treatment group. Change in ejection fraction (EF) was calculated as: (EF at day 49)−(EF at day 21)]/(EF at day 21).

Histologic Analyses:

To obtain cardiac tissue specimens, animals were exsanguinated under deep anesthesia via an incision made in the right atrium. While the heart was still beating, it was perfused with normal saline and fixed with phosphate-buffered saline (pH 7.2) containing 4% (w/v) paraformaldehyde via a 25 gauge needle inserted into the left ventricular apex. The heart was then harvested and rinsed with saline to clear the blood. Excised hearts were fixed with 4% paraformaldehyde for 24 h, and then 2% paraformaldehyde for 48 h at 4° C. The heart was then cut transversally and sectioned to obtain two (2-3 mm) slices, one immediately cephalad and one immediately caudad to the transverse centerline of the infarct region, which was readily identifiable by gross inspection. After paraffin embedding of these slices, seven 5 µm thick sections were obtained at 90 µm intervals.

For analyses of in vivo cellular reprogramming, microscopic slides of every other section obtained as described above were stained with primary antibodies against beta myosin heavy chain 7 (anti-MYH7, Sigma), then incubated with secondary IgG antibody. Five microscopic fields per slide (at the center of the infarction zone, in the mid areas between the center of infarction and the border zone [left and right], and in each border zone adjacent to the infarct [left and right]) viewed at 200× magnification were graded semi-quantitatively in order to determine MYH7$^+$ cell density. Density grading assessed by an investigator blinded to treatment group were defined as follows: Grade I: <25% of selected microscopic field demonstrating MYH7$^+$ cells/; Grade II: 25%-50% of selected microscopic field demonstrating MYH7$^+$ cells; Grade III: 50%-75% of selected microscopic field demonstrating MYH7$^+$ cells; and Grade IV: >75% of selected microscopic field demonstrating MYH7$^+$ cells (FIG. 7).

These observations are reported as the percentage of fields per animal demonstrating a given density grade, and the mean of these percentages per group for all animals with at least ten fields analyzable within an infarct zone.

To assess the extent of fibrosis, 22 sections per animal (at a 120 µm interval between each section) obtained as described above were stained with Masson's trichrome. The fibrotic area (blue) and the non-fibrotic region (red) were outlined using Adobe PHOTOSHOP™ CS5 software, and then quantified with MATLAB & SIMULINK software (Math Works, Inc). The total area of fibrosis was calculated as: [total of blue pixels from all sections/total of blue plus red pixels from all sections].

For myofibroblast identification, two sections per animal demonstrating the greatest cross sectional area of fibrosis, as determined by trichrome staining, were stained for α-smooth muscle actin (Anti-Actin-Smooth Muscle, Spring Bioscience [α-SMA]). α-SMA-positive cells in these sections exclusive of those found in vascular structures or endocardium were counted at 200× magnification.

For vascularization studies, the number of vessels per microscopic field was determined from the sections stained as above with α-SMA, or with Factor VIII (anti-Factor VIII-related antigen, Ventana) and counted at 200× or 400×, respectively.

Statistical Analysis:

Statistical analysis was performed with SAS, 9.2. The data is presented as mean±standard error of the mean. The normality of the data was examined with Shapiro-Wilk. When there was a normal distribution, an ANOVA test was performed to detect statistical significances between multiple groups. When the ANOVA test showed significance, a student t-test was performed with a post hoc Holm-Bonferroni correction. When there was not a normal distribution, a Kruskal-Wallis test was performed. When the test was significant, the Wilcoxon rank test was performed with a post-hoc Holm-Bonferroni correction. For categorical variables, a Fischer exact test was performed. Values of p<0.05 were considered statistically significant.

In Vitro iCM Generation:

The competency of each of the GMT lentivirus vectors was confirmed by in vitro cell infection assays, which demonstrated expression of all three of the reprogramming transcription factors (FIG. 1). Confirmation of the ability of these transcription factors to induce iCM transdifferentiation was obtained by immunofluorescence staining of rat dermal fibroblasts following GMT lentiviral transduction. In these studies, cells exposed to GMT vectors expressed cardiomyocyte-specific markers including cardiac troponin T (cTnT), alpha sarcomeric actin, and beta myosin heavy chain (MYH) 7, while uninfected cells and fibroblasts exposed only to a GFP control vector failed to express these markers (FIG. 2A). By FACS quantification, GMT infection demonstrated evidence of cardiomyocyte marker expression by approximately 7% of infected fibroblasts (FIGS. 2B-F).

Figure 10B:
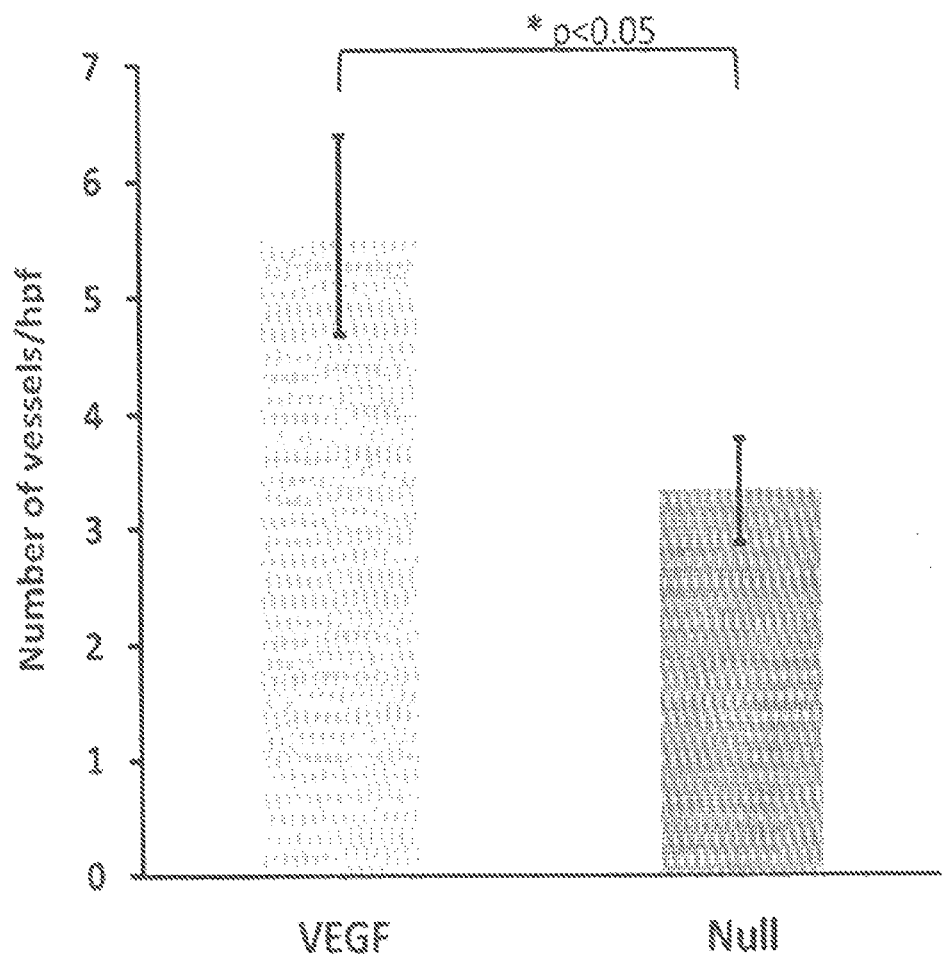

Vascularization of Infarcted Myocardium:

Vascularization of the infarct region as assessed by α-SMA staining was significantly greater in AdVEGF-All6A$^+$ treated animals compared to animals receiving an AdNull control vector: 5.5±0.9 versus 3.3±0.4, respectively; p<0.05 (FIG. 3; FIG. 8). A similar, approximate two-fold increase in vessels stained with Factor VIII was noted in animals receiving AdVEGF-All6A$^+$ alone versus those receiving AdNull alone (14.1±2.1 versus 7.3±1.4, p<0.05). Also see FIGS. 10A-B.

Histologic Assessment of Post-Infarct Ventricles:

In order to assess the efficacy of GMT administration with or without VEGF pre-treatment in vivo, a series of histologic analyses were performed on sections of the heart obtained 4 wks following GMT/GFP delivery (7 wks following coronary ligation and AdVEGF-All6A$^+$/AdNull administration). These studies demonstrated a greater density of cells staining for the cardiomyocyte marker MYH7 in the infarct zone in GMT-treated animals compared to control animals (FIGS. 4A-D). Typically, GMT-treated animals demonstrated relatively large islands of MYH7$^+$ cells, compared to sparse foci of MYH7$^+$ in control animals.

Using a Grade I-IV scale to semi-quantitatively assess MYH7 cell density, GMT treated animals demonstrated Grade III/IV MYH7 cell density in the infarct zone in a greater percentage of microscopic fields than did GFP control animals, both in the infarct zone and border zones (Table 2).

TABLE 2

| MYH7$^+$cell density* | | | | |
|---|---|---|---|---|
| | Grade I$^†$ | Grade II$^†$ | Grade III$^†$ | Grade IV$^†$ |
| Infarction Area | | | | |
| AdVEGF-A116A$^+$/GMT | 12 ± 5 | 44 ± 8 | 30 ± 7 | 14 ± 5 |
| AdNull/GMT | 29 ± 13 | 41 ± 8 | 22 ± 7 | 8 ± 5 |
| AdVEGF-A116A$^+$/ GFP | 61 ± 14 | 34 ± 13 | 5 ± 3 | 0 |
| AdNull/GFP | 50 ± 14 | 40 ± 10 | 10 ± 6 | 0 |
| Border Zone Area | | | | |
| AdVEGF-A116A$^+$/GMT | 4 ± 3 | 29 ± 9 | 48 ± 10 | 19 ± 7 |
| AdNull/GMT | 14 ± 10 | 24 ± 7 | 38 ± 9 | 25 ± 10 |

TABLE 2-continued

| MYH7$^+$cell density* | | | | |
|---|---|---|---|---|
| | Grade I$^†$ | Grade II$^†$ | Grade III$^†$ | Grade IV$^†$ |
| AdVEGF-A116A$^+$/ GFP | 30 ± 14 | 48 ± 11 | 21 ± 12 | 1 ± 1 |
| AdNull/GFP | 43 ± 13 | 32 ± 7 | 22 ± 10 | 3 ± 2 |

Figure 4A:
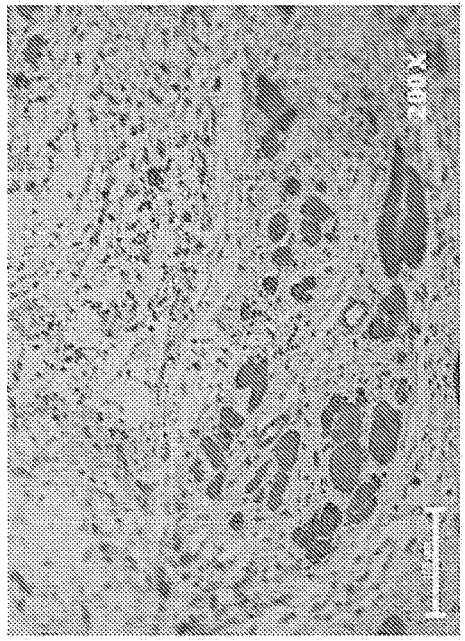
FIGS. 4A-E are a set of photographs and graphs showing cardiomyocyte density in infarct zones. Cardiomyocyte-specific marker MYH7 staining of the infarct and border zones of sections of myocardium harvested 7 wks following coronary ligation and administration of AdVEGF-All6AP+P or the control vector AdNull (4 wks after the administration of lentivirus encoding GMT or a GFP control) was performed.
Figure 4B:
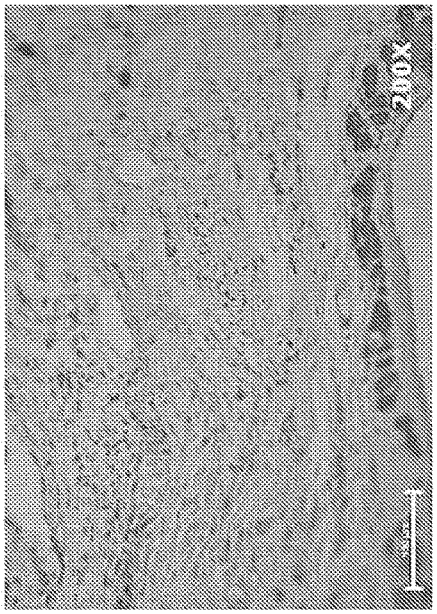
Figure 4C:
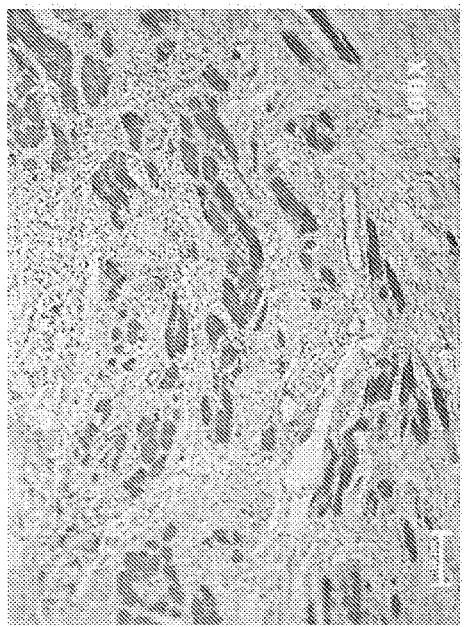
Figure 4D:
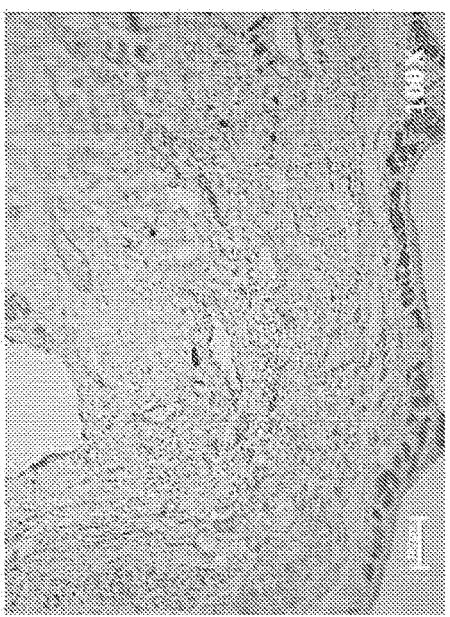
Figure 4E:
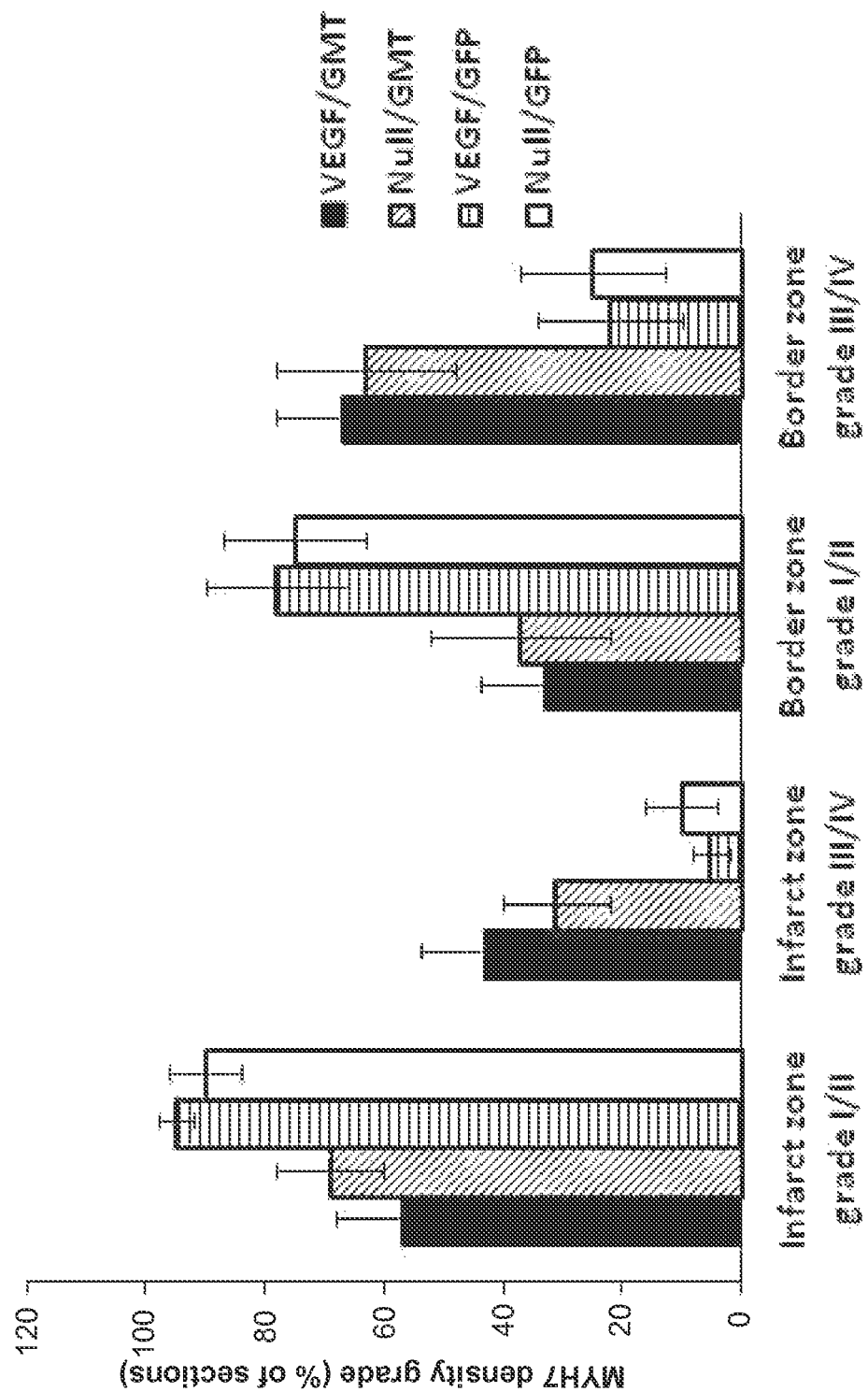
Figure 11B:
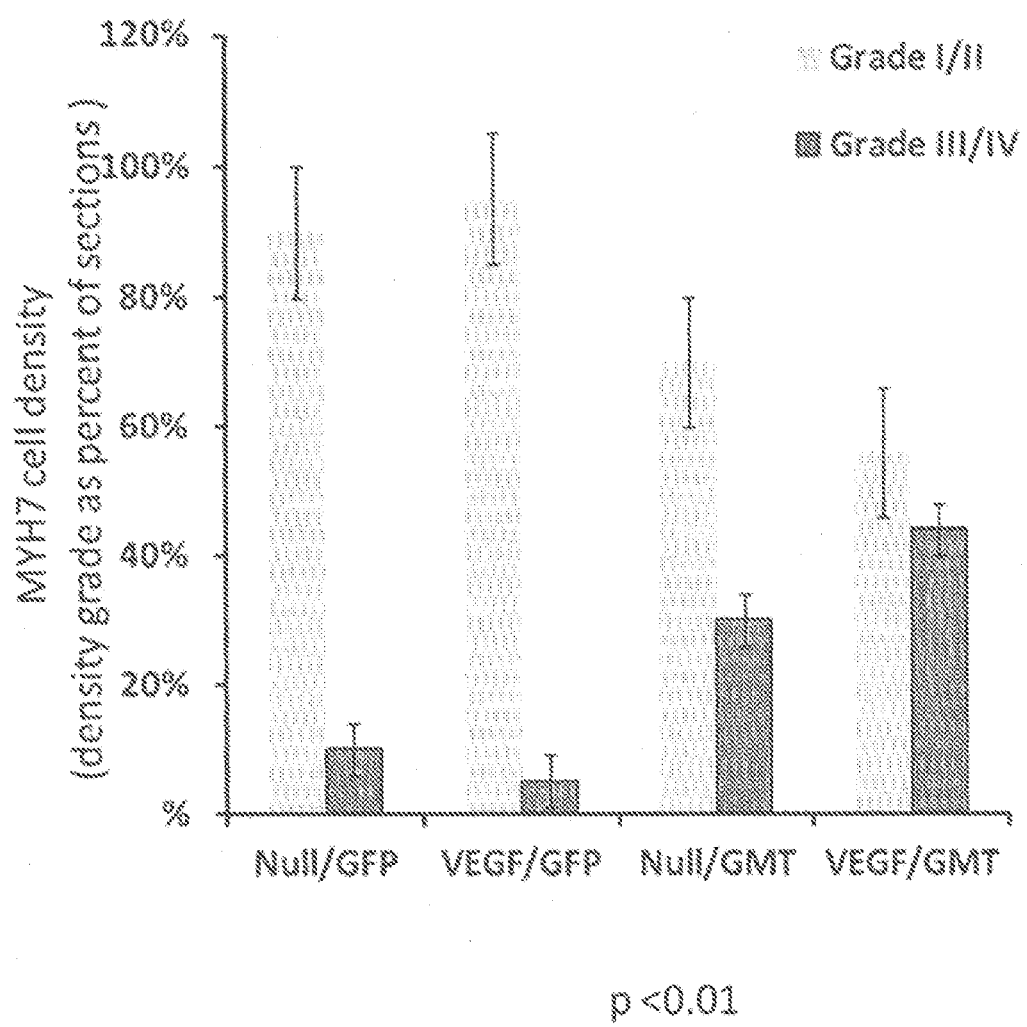

*Percent of microscopic fields analyzed demonstrating density grade (n = 6 animals per treatment group).
$^†$Grade I: <25% of microscopic field containing MYH7$^+$cells: Grade II: 25%-50% of microscopic field containing MYH7$^+$cells, Grade III: 50%-75% of microscopic field containing MYH7$^+$cells; Grade IV: >75% of microscopic field containing MYH7$^+$cells. All measurements at 200X The percentage of microscopic fields demonstrating Grade III/IV MYH7 cell density was significantly greater in GMT-treated animals compared to GFP-treated control animals (36%±8% versus 7%±4%, p<0.01) in the infarct zone and in the border zones adjacent to these infarct zones (65%±10% versus 23%±9%, p<0.01). Notably, none of the sections demonstrated Grade IV MYH7 cell density in the infarct zone in the GFP control groups. The administration of AdVEGF-All6A$^+$ did not appear to alter MYH7 cell density (FIG. 4E). Also see FIGS. 11A-B.

Figure 5A:
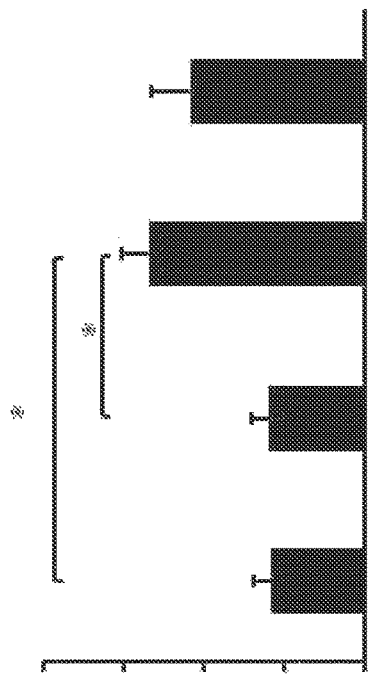
FIGS. 5A-C are a set of graphs showing the extent of left ventricular wall fibrosis. The percent of left ventricular myocardial wall area demonstrating fibrosis as determined by trichrome staining of sections of myocardial tissue harvested 7 wks following coronary ligation and administration of AdVEGF-All6AP+P or the control vector AdNull (4 wks after the administration of lentivirus encoding GMT or a GFP control) animals is depicted.
Figure 5B:
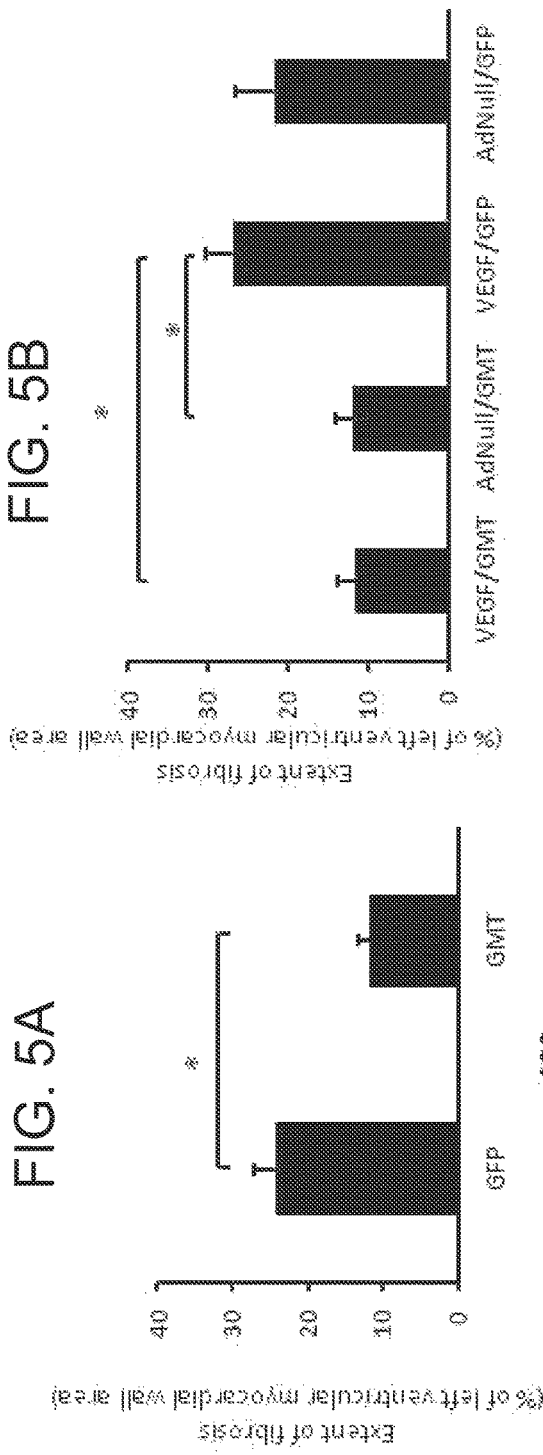
Figure 12A:
FIGS. 12A-B are a set of photographs (FIG. 12A) and graphs (FIG. 12B) showing the extent of fibrosis.
Figure 12B:
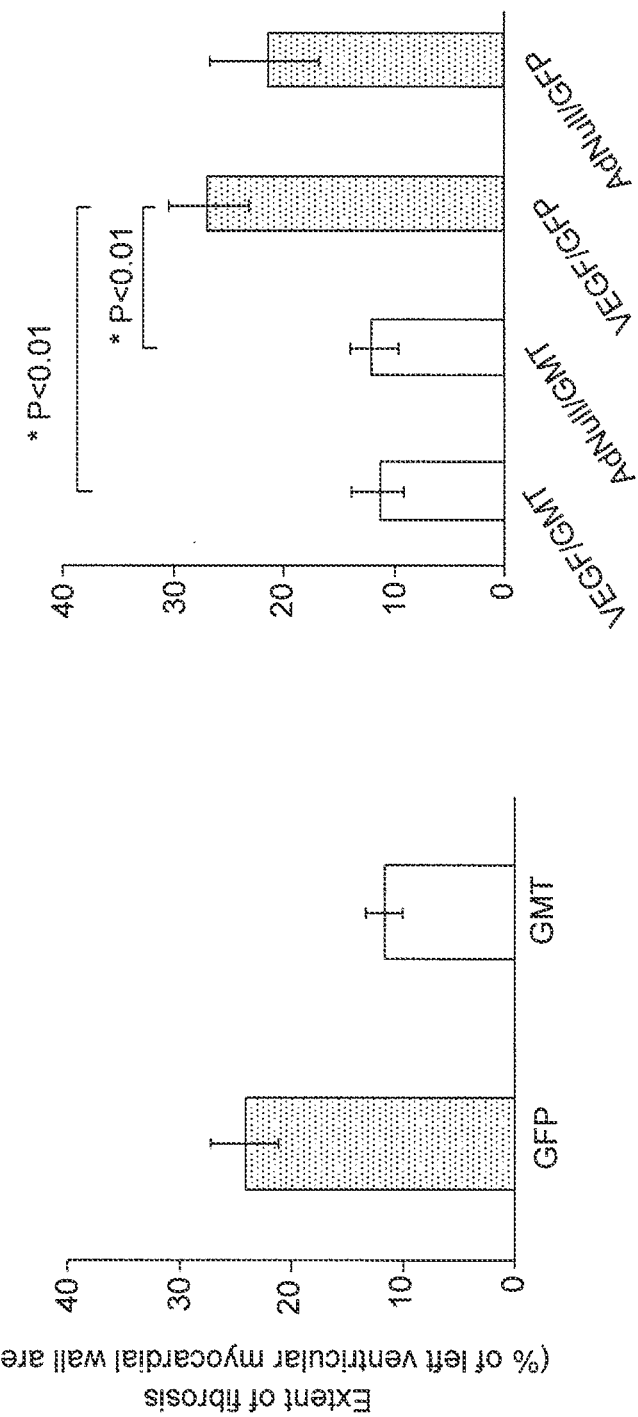

The extent of fibrosis in these sections, as detected by trichrome staining, was also significantly reduced in GMT-treated animals compared to those receiving GFP, regardless of VEGF administration (FIG. 5A). The cross sectional area of fibrosis in these groups, as a percentage of total left ventricular myocardial area in sections analyzed, was 12%±2% versus 24%±3%, (p<0.01). No difference in the extent of fibrosis was detected in animals treated with AdVEGF-All6A$^+$ without GMT compared to AdNull/GFP controls (FIG. 5B). Also, AdVEGF-All6A$^+$ administration did not further reduce the extent of fibrosis compared to animals treated with GMT without VEGF. Also see FIGS. 12A-B.

Figure 5C:
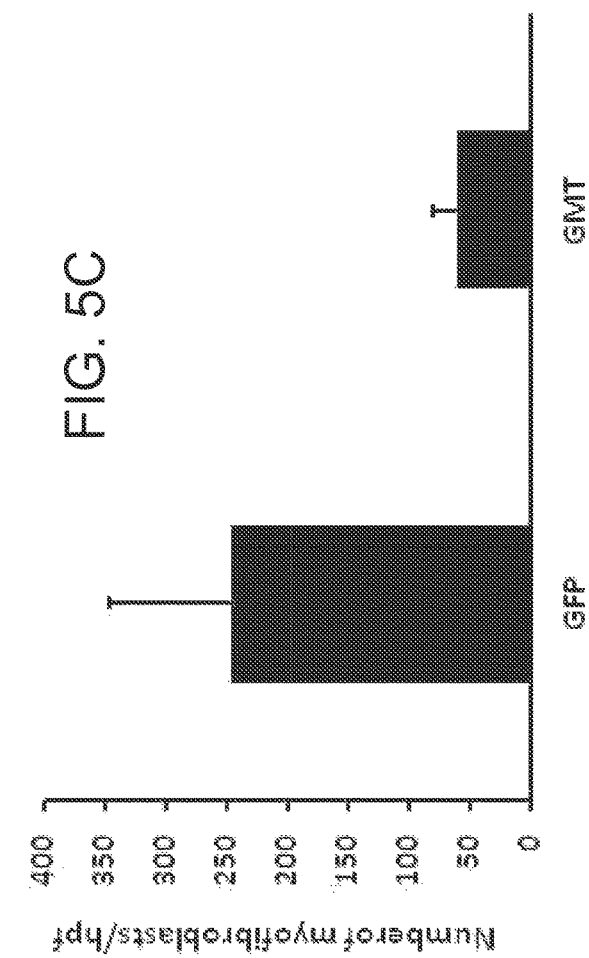

Consistent with the reduction in fibrosis detected in GMT-treated animals, there was approximately a four-fold decrease in the number of myofibroblasts observed in GMT-treated animals compared to control animals, regardless of VEGF administration (FIG. 5C; FIG. 9).

Improvement in Ventricular Function Following GMT and VEGF Administration:

Echocardiography was performed to assess the functional implications of the outcomes noted above. Echo analyses performed before and immediately after coronary ligation demonstrated that ejection fraction was reduced by approximately 30% from baseline values (FIG. 6A). This decrease in cardiac function persisted 3 wks later, at the time of GMT or GFP lentivirus administration.

As detailed in Table 3, mean ejection fraction 4 wks after GMT or GFP administration was greatest for animals receiving GMT administration with AdVEGF-All6A$^+$ pretreatment (AdVEGF-All6A$^+$/GMT), being significantly greater than animals receiving either AdVEGF-All6A$^+$ without GMT (AdVEGF-All6A$^+$/GFP; p<0.05) or both control vectors (AdNull/GFP; p<0.05).

TABLE 3

| Ejection fraction group means as assessed by echocardiography* | | | | | |
|---|---|---|---|---|---|
| | Time (days)$^†$ | | | | |
| Group | 0 | 3 | 21 | 35 | 49 |
| AdVEGF-A116A$^+$/GMT | 75 ± 2 | 55 ± 3 | 54 ± 2 | 65 ± 2 | 63 ± 2$^{‡§∥}$ |
| AdNull/GMT | 75 ± 1 | 56 ± 3 | 53 ± 2 | 61 ± 3 | 56 ± 2$^∥$ |

TABLE 3-continued

Ejection fraction group means as assessed by echocardiography*

| Group | Time (days)† | | | | |
|---|---|---|---|---|---|
| | 0 | 3 | 21 | 35 | 49 |
| AdVEGF-A116A+/GFP | 76 ± 1 | 51 ± 3 | 51 ± 2 | 53 ± 4 | 51 ± 2§# |
| AdNull/GFP | 74 ± 1 | 51 ± 2 | 53 ± 3 | 52 ± 8 | 48 ± 2‡# |

*All data expressed as a percent ejection fraction (n = 6 animals per treatment group)
†Day 0 represents time of coronary ligation and AdVEGF-A116A or AdNull administration; day 21 represents time of administration of lentivirus encoding GMT or GFP
‡AdVEGF-A116A+/GMT versus AdNull/GFP at 49 d: $p < 0.05$
§AdVEGF-A116A+/GMT versus AdVEGF-A116A+/GFP at 49 d: $p < 0.05$
∥AdVEGF-A116A+/GMT versus AdNull/GMT at 49 d: $p = 0.08$
AdVEGF-A116A+/GFP versus AdNull/GFP at 49 d: $p = 0.86$ Similar observations were made for differences between groups in fractional shortening (Table 4).

TABLE 4

Ventricular functional metrics as assessed by echocardiography*

| Parameter | Time (days)† | | | | |
|---|---|---|---|---|---|
| | 0 | 3 | 21 | 35 | 49 |
| End diastolic volume‡ | | | | | |
| AdVEGF-A116A+/GMT | 217 ± 7 | 181 ± 13 | 215 ± 17 | 222 ± 21 | 234 ± 25 |
| AdNull/GMT | 206 ± 8 | 147 ± 18 | 239 ± 12 | 208 ± 16 | 231 ± 23 |
| AdVEGF-A116A+/GFP | 192 ± 11 | 197 ± 11 | 302 ± 30 | 240 ± 32 | 280 ± 32 |
| AdNul/GFP | 207 ± 13 | 193 ± 19 | 262 ± 17 | 265 ± 32 | 252 ± 26 |
| End systolic volume | | | | | |
| AdVEGF-A116A+/GMT | 54 ± 5 | 80 ± 7 | 99 ± 10 | 80 ± 11 | 84 ± 7 |
| AdNull/GMT | 51 ± 2 | 65 ± 5 | 112 ± 10 | 81 ± 10 | 105 ± 14 |
| AdVEGF-A116A+/GFP | 47 ± 3 | 97 ± 8 | 148 ± 17 | 117 ± 23 | 139 ± 20 |
| AdNull/GFP | 54 ± 4 | 95 ± 11 | 123 ± 11 | 131 ± 23 | 134 ± 18 |
| Fractional shortening | | | | | |
| AdVEGF-A116A+/GMT | 45 ± 2 | 30 ± 2 | 29 ± 1 | 36 ± 2 | 35 ± 1§∥# |
| AdNull/GMT | 45 ± 1 | 29 ± 2 | 28 ± 1 | 34 ± 2 | 30 ± 1§** |
| AdVEGF-A116A+/GFP | 46 ± 1 | 27 ± 2 | 27 ± 1 | 28 ± 2 | 27 ± 1∥ |
| AdNull/GFP | 44 ± 1 | 27 ± 1 | 28 ± 2 | 27 ± 2 | 25 ± 1#** |

*All data expressed as a percent ejection fraction (n = 6 animals per treatment group)
†Day 0 represents time of coronary ligation and AdVEGF-A116A or AdNull administration; day 21 represents time of administration of lentivirus encoding GMT or GFP
‡No significant difference between groups at any time interval.
§AdVEGF-A116A+/GMT vs. AdNull/GMT: $p = 0.08$
∥AdVEGF-A116A+/GMT vs. AdVEGF-A116A+/GFP: $p < 0.01$
AdVEGF-A116A+/GMT vs. AdNull/GFP: $p < 0.0001$
**AdNull/GMT vs. AdNull/GFP: $p = 0.07$ When grouped together regardless of prior AdVEGF administration, GMT-treated animals demonstrated significantly greater mean ejection fraction compared to similarly combined GFP control animals, both at 2 wks and at 4 wks following lentivirus administration (2 wks: 63%±2% versus 52%±2%, $p<0.01$); 4 wks: 60%±2% versus 49%±2%, $p<0.001$). In comparison, no difference in ejection fraction was seen following AdVEGF-A116A+ administration alone (without GMT) versus animals receiving control vectors.

Figure 6B:
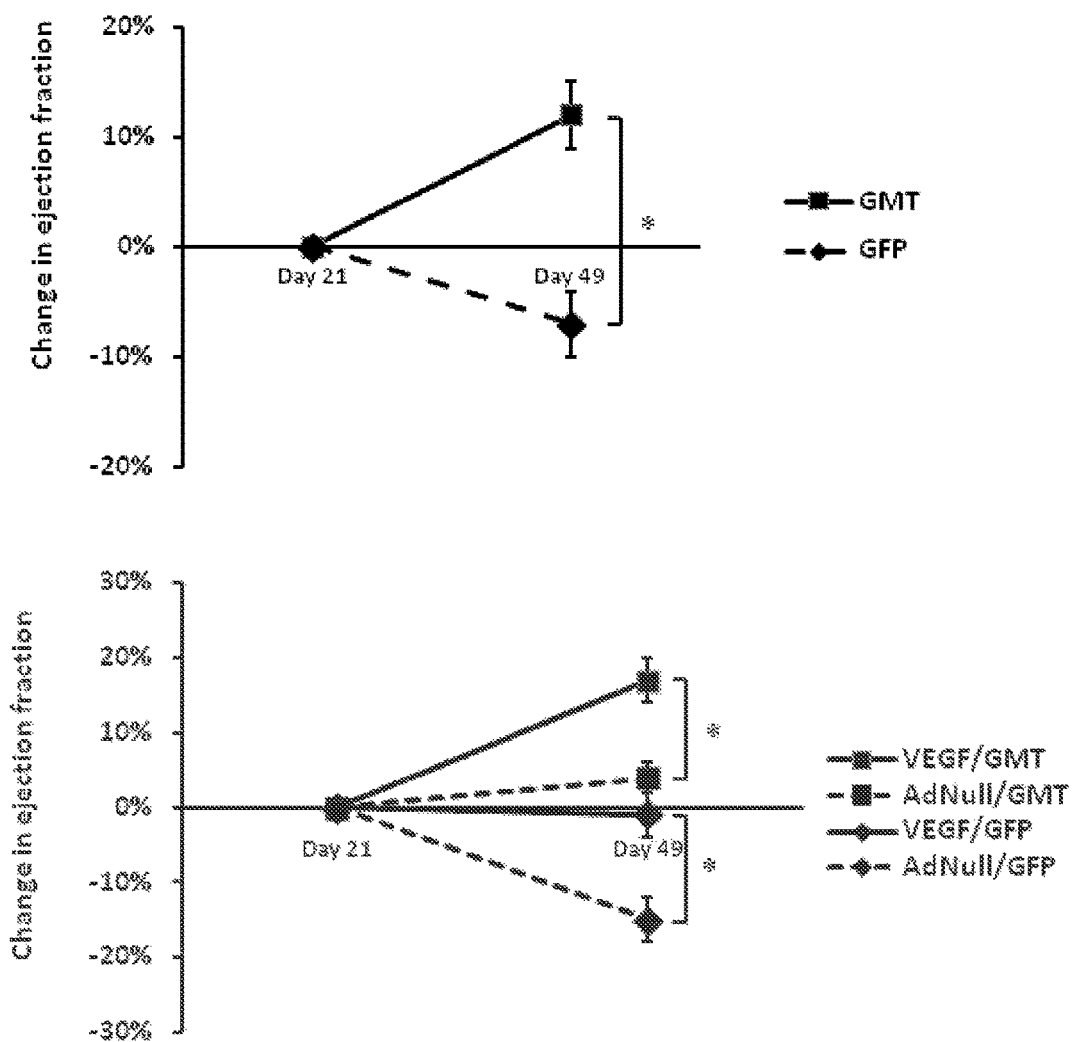

The change in ejection fraction from the time of the lentivirus administration baseline to the time of follow up echo 4 wks later (FIG. 6B, top panel) was also greater in the GMT versus GFP groups (12%±3% versus −7%±3%, $p<0.01$). Eight (73%) GFP-treated animals, but none of the GMT animals, demonstrated decreased ejection fraction during this interval ($p<0.01$). Moreover, as depicted in FIG. 6B (bottom panel), the improvement in ejection fraction observed in the AdVEGF-A116A+/GMT group was four times greater than that observed for the AdNull/GMT group (17%±2% versus 4%±1%, $p<0.05$), and was significantly greater ($p=0.008$) than the change in ejection fraction observed after administration of VEGF alone (AdVEGF-A116A+/GFP).

Figure 6C:
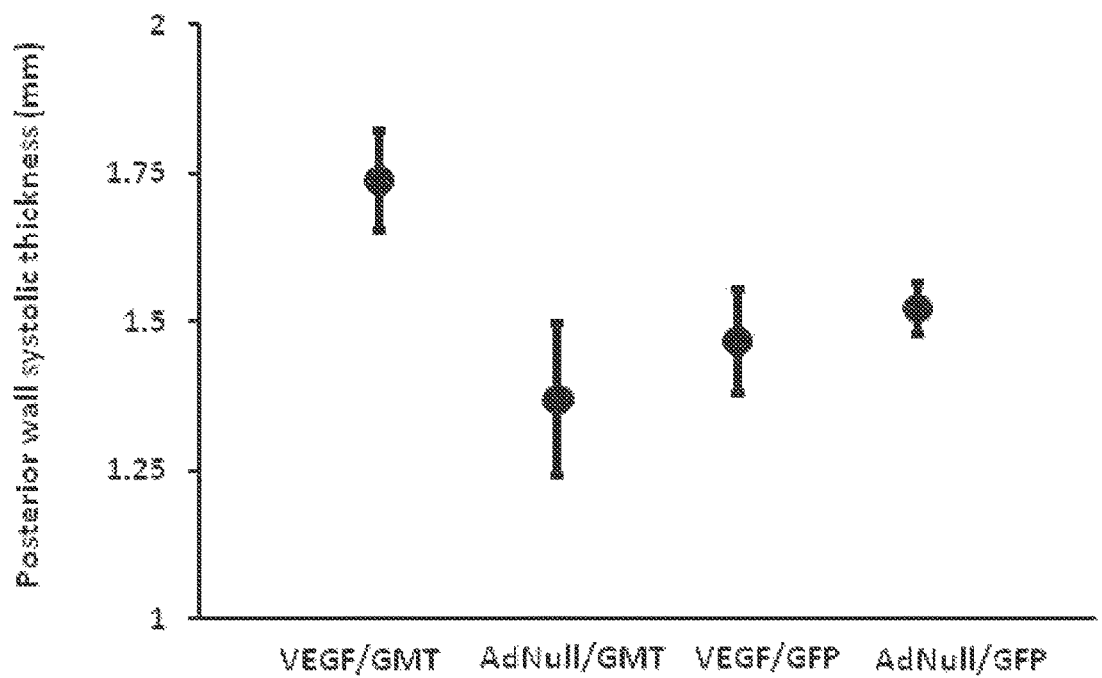

Interestingly, systolic wall thickening of the (remote, non-injected) left ventricular posterior wall also trended towards greater values in the GMT/VEGF group compared to animals receiving GMT without VEGF and compared to GFP/AdNull controls (FIG. 6C).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating coronary artery disease in a mammal with the coronary artery disease, the method comprising administering directly to a region of the heart of the mammal
   (a) a first expression vector comprising a promoter operably linked to a nucleic acid sequence encoding VEGF, and
   (b) a second expression vector comprising a promoter operably linked to a nucleic acid sequence encoding Gata4, Mef2c, and Tbx5 (GMT),
whereby the coronary artery disease in the mammal is treated.

2. The method of claim 1, wherein the first expression vector is an adenoviral vector.

3. The method of claim 2, wherein the adenoviral vector is of serotype 5 and has deletions in the E1 and E3 regions.

4. The method of claim 1, wherein the second expression vector is a lentiviral vector.

5. The method of claim 1, wherein the region of the heart is a myocardial scar or peri-infarcted region of the heart.

6. The method of claim 1, wherein the coronary artery disease is myocardial infarction.

7. The method of claim 1, wherein the first expression vector is administered at the same time as the second expression vector.

8. The method of claim 1, wherein the first expression vector is an adenoviral vector, and the second expression vector is a lentiviral vector.

9. A method of treating coronary artery disease in a mammal with the coronary artery disease, the method comprising administering directly to a region of the heart of the mammal
   (a) a first expression vector comprising a promoter operably linked to a nucleic acid sequence encoding VEGF, and
   (b) a second expression vector comprising a promoter operably linked to a nucleic acid sequence encoding Gata4, Mef2c, and Tbx5 (GMT),
   wherein the first expression vector is administered before the second expression vector,
   whereby the coronary artery disease in the mammal is treated.

10. The method of claim 9, wherein the first expression vector is administered about 3 weeks before the second expression vector.

* * * * *

```
                           SEQUENCE LISTING

<160> NUMBER OF SEQ ID NOS: 6

<210> SEQ ID NO 1
<211> LENGTH: 31
<212> TYPE: DNA
<213> ORGANISM: Artificial Sequence
<220> FEATURE:
<223> OTHER INFORMATION: Synthetic primer

<400> SEQUENCE: 1
ggcggtcgac atgtaccaaa gcctggctat g                                   31

<210> SEQ ID NO 2
<211> LENGTH: 33
<212> TYPE: DNA
<213> ORGANISM: Artificial Sequence
<220> FEATURE:
<223> OTHER INFORMATION: Synthetic primer

<400> SEQUENCE: 2
gattctcgag tacgcggtga ttatgtcccc atg                                 33

<210> SEQ ID NO 3
<211> LENGTH: 32
<212> TYPE: DNA
<213> ORGANISM: Artificial Sequence
<220> FEATURE:
<223> OTHER INFORMATION: Synthetic primer

<400> SEQUENCE: 3
ggactgtcga catggggaga aaaagattc ag                                   32

<210> SEQ ID NO 4
<211> LENGTH: 35
<212> TYPE: DNA
<213> ORGANISM: Artificial Sequence
<220> FEATURE:
<223> OTHER INFORMATION: Synthetic primer

<400> SEQUENCE: 4
tgtgactcga gtcatgttgc ccatccttca gagag                               35

<210> SEQ ID NO 5
<211> LENGTH: 28
<212> TYPE: DNA
<213> ORGANISM: Artificial Sequence
<220> FEATURE:
<223> OTHER INFORMATION: Synthetic primer

<400> SEQUENCE: 5
caccgtcgac atggccgacg cagatgag                                       28

<210> SEQ ID NO 6
<211> LENGTH: 34
```

```
<212> TYPE: DNA
<213> ORGANISM: Artificial Sequence
<220> FEATURE:
<223> OTHER INFORMATION: Synthetic primer

<400> SEQUENCE: 6
ccttctcgag tcaagctatt ctcgctccac tctg                          34
```